US011992479B2

(12) United States Patent
Steele et al.

(10) Patent No.: US 11,992,479 B2
(45) Date of Patent: *May 28, 2024

(54) R-FADROZOLE FOR USE IN THE TREATMENT OF ALDOSTONERISM

(71) Applicant: DAMIAN PHARMA AG, Walchwil (CH)

(72) Inventors: Ronald Edward Steele, Long Valley, NJ (US); Christoph Schumacher, Walchwil (CH)

(73) Assignee: DAMIAN PHARMA AG, Walchwil (CH)

( * ) Notice: Subject to any disclaimer, the term of this patent is extended or adjusted under 35 U.S.C. 154(b) by 76 days.

This patent is subject to a terminal disclaimer.

(21) Appl. No.: 17/052,359

(22) PCT Filed: May 2, 2019

(86) PCT No.: PCT/EP2019/061283
§ 371 (c)(1),
(2) Date: Nov. 2, 2020

(87) PCT Pub. No.: WO2019/211394
PCT Pub. Date: Nov. 7, 2019

(65) Prior Publication Data
US 2021/0169861 A1 Jun. 10, 2021

Related U.S. Application Data

(60) Provisional application No. 62/666,412, filed on May 3, 2018.

(30) Foreign Application Priority Data

Jun. 6, 2018 (EP) .................................... 18176345

(51) Int. Cl.
A61K 31/473 (2006.01)
A61K 31/437 (2006.01)
A61P 5/00 (2006.01)

(52) U.S. Cl.
CPC ............. A61K 31/437 (2013.01); A61P 5/00 (2018.01)

(58) Field of Classification Search
CPC ................. A61K 31/437; A61P 5/00
See application file for complete search history.

(56) References Cited

U.S. PATENT DOCUMENTS

| 5,057,521 | A | 10/1991 | Hausler |
| 5,098,911 | A | 3/1992 | Ibrahim |
| 5,428,160 | A | 6/1995 | Browne |
| 10,822,332 | B2 | 11/2020 | Schumacher et al. |
| 11,447,491 | B2 | 9/2022 | Schumacher et al. |
| 2009/0105278 | A1 | 4/2009 | Hartmann et al. |

FOREIGN PATENT DOCUMENTS

| EP | 1 886 695 A1 | 2/2008 |
| NZ | 534086 A | 8/2006 |
| WO | 2001/76574 A2 | 10/2001 |
| WO | 2005/099695 A1 | 10/2005 |
| WO | WO2005/099695 A1 * | 10/2005 |
| WO | 2007/024945 A1 | 3/2007 |
| WO | 2013/109514 A1 | 7/2013 |
| WO | 2016/005880 A1 | 1/2016 |
| WO | 2018/078049 A1 | 5/2018 |

OTHER PUBLICATIONS

Menard & Pascoe, 24(6) J. Hypertension 993-997 (2006) (Year: 2006).*
International Search Report dated Jul. 16, 2019, in International Appl. No. PCT/EP2019/061283.
Azizi et al., "Aldosterone synthase inhibition in humans," Nephrology Dialysis Transplantation 28(1): 36-43 (2013).
Menard et al., "Can the dextroenantiomer of the aromatase inhibitor fadrozole be useful for clinical investigation of aldosterone-synthase inhibition?", Journal of Hypertension 24(6):993-997 (2006).
Minnaard-Huiban et al., "Fadrozole Reverses Cardiac Fibrosis in Spontaneously Hypertensive Heart Failure Rats: Discordant Enantioselectively Versus Reduction of Plasma Aldosterone," Endocrinology 149(1):pp. 28-31 (2008).
Browne et al., "Fadrozole hydrochloride: a potent, selective, nonsteroidal inhibitor of aromatase for the treatment of estrogen-dependent disease," J. Med. Chem. 34:725-736 (1991).
Fiebeler et al., "Aldosterone synthase inhibitor ameliorates angiotensin II—induced organ damage," Circulation 111:3087-3094 (2005).

(Continued)

Primary Examiner — Timothy R Rozof
(74) Attorney, Agent, or Firm — MEDLER FERRO WOODHOUSE & MILLS PLLC

(57) ABSTRACT

The present invention relates to a composition for use in the treatment of a disease or disorder, wherein said disease or disorder is preferably a disease or disorder in which aldosterone overexposure contributes to the symptoms of said disease or disorder, said composition comprises a compound which is (R)-(+)-5-(p-cyanophenyl)-5,6,7,8-tetrahydroimidazo[1,5-a]pyridine or a pharmaceutically acceptable salt thereof, wherein preferably said compound is (R)-(+)-5-(p-cyanophenyl)-5,6,7,8-tetrahydroimidazolium[1,5-a]pyridine dihydrogen phosphate, and wherein said compound has an enantiomeric excess (ee) of the (R) form higher than or equal to 97%, and wherein said composition is administered once daily to a subject in need thereof. The invention further relates to a pharmaceutical composition comprising a daily dosage of said compound in a fixed-unit dosage form and to a combination comprising (i) said pharmaceutical composition or said compound; and (ii) instructions for administration of said pharmaceutical composition or said compound once per day.

18 Claims, No Drawings

(56) References Cited

OTHER PUBLICATIONS

Furet et al., "Aromatase inhibitors: synthesis, biological activity, and binding mode of azole-type compounds," J. Med Chem. 36:1393-1400 (1993).
Hojo et al., "Adult male rat hippocampus synthesizes estradiol from pregnenolone by cytochromes P45017α and P450 aromatase localized in neurons," PNAS 101(3):865-870 (2004).
Kandasamy et al., "Possible existence of the hypothalamic-pituitary-hippocampal (HPH) axis: a reciprocal relationship between hippocampal specific neuroestradiol synthesis and neuroblastosis in ageing brains with special reference to menopause and neurocognitive disorders," Neurochem. Res. 44:1781-1795 (2019).
Martin et al., "Discovery of 4-Aryl-5, 6, 7, 8-tetrahydroisoquinolines as potent, selective, and orally active aldosterone synthase (CYP11B2) inhibitors: in vivo evaluation in rodents and cynomolgus monkeys," J. Med. Chem. 58:8054-8065 (2015).
Menard et al., "Investigation of aldosterone-synthase inhibition in rats," Journal of Hypertension, 24(6):1147-1155 (2006).
Roumen et al., "Construction of 3D models of the CYP11B family as a tool to predict ligand binding characteristics," J. Comp. Aided Mol. Des. 21(8):455-471 (2007).
International Search Report mailed Nov. 27, 2017, in PCT/EP2017/077511.
Amar et al., "Aldosterone synthase inhibition with LCI699: a proof-of-concept study in patients with primary aldosteronism," Hypertension 56:831-838 (2010).
Briones et al., "Adipocytes produce aldosterone through calcineurin-dependent signaling pathways: implications in diabetes mellitus-associated obesity and vascular dysfunction," Hypertension 59(5):1069-1078 (2012).
Brunssen et al., "Impact of aldosterone synthase inhibitor FAD286 on steroid hormone profile in human adrenocortical cells," Horm Metab Res 49(9):701-706 (2017).
Deliyanti et al., "Neovascularization is attenuated with aldosterone synthase inhibition in rats with retinopathy," et al., Hypertension 59(3):607-13 (2012).
Funder, "Trilostane, FAD286, and the role of aldosterone in the central regulation of blood pressure: focus on Role of central nervous system aldosterone synthase and mineralocorticoid receptors in salt-induced hypertension in Dahl salt-sensitive rats," Am J Physiol Regul Integr Comp Physiol. 296(4):R992-3 (2009).
Funder et al., "The Management of Primary Aldosteronism: Case Detection, Diagnosis, and Treatment: An Endocrine Society Clinical Practice Guideline," J. Clinical Endocrinology & Metabolism 101(5):1889-1916 (2016).
Gamliel-Lazarovich et al., "FAD286, an aldosterone synthase inhibitor, reduced atherosclerosis and inflammation in apolipoprotein E-deficient mice," J Hypertens. 28(9):1900-1907 (2010).
Gomez-Sanchez et al., "Aldosterone synthesis in the brain contributes to Dahl salt-sensitive rat hypertension," Exp Physiol. 95(1):120-130 (2010).
Hamlyn et al., "Neuroendocrine humoral and vascular components in the pressor pathway for brain angiotensin II: a new axis in long term blood pressure control," PLos One 9(10):e108916 (2014).
Hofmann et al., "The aldosterone synthase inhibitor FAD286 is suitable for lowering aldosterone levels in ZDF rats but not in db/db mice," Horm Metab Res 49(6):466-471 (2017).
Hofmann et al., "Aldosterone synthase inhibition improves glucose tolerance in Zucker diabetic fatty (ZDF) rats," Endocrinology 157(10):3844-3855 (2016).

Huang et al., "Central infusion of aldosterone synthase inhibitor prevents sympathetic hyperactivity and hypertension by central Na$^+$ in Wistar rats," Am J Physiol Regul Integr Comp Physiol. 295(1):R166-R172 (2008).
Huang et al., "Central infusion of aldosterone synthase inhibitor attenuates left ventricular dysfunction and remodelling in rats after myocardial infarction," Cardiovasc Res. 81(3):574-581 (2009).
Huang et al., "Role of central nervous system aldosterone synthase and mineralocorticoid receptors in salt-induced hypertension in Dahl salt-sensitive rats," Am J Physiol Regul Integr Comp Physiol. 296(4):R994-R1000 (2009).
Huang et al., "Role of brain corticosterone and aldosterone in central angiotensin II-induced hypertension," Hypertension 62(3):564-571 (2013).
Kawarazaki et al. "Mineralocorticoid receptor activation: a major contributor to salt-induced renal injury and hypertension in young rats," Am J Physiol Renal Physiol. 300(6): F1402-F1409 (2011).
Korte et al., "Feedforward activation of endothelial ENaC by high sodium," Faseb J 28(9):4015-4025 (2014).
LaSala et al., "Co-expression of CYP11B2 or CYP11B1 with adrenodoxin and adrenodoxin reductase for assessing the potency and selectivity of aldosterone synthase inhibitors," Anal Biochem. 394(1):56-61 (2009).
Launonen et al., "Adverse effects of an aldosterone synthase (CYP11B2) inhibitor, fadrozole (FAD286), on inflamed rat colon," Basic Clin Pharmacol Toxicol 133(3):211-225 (2023).
Lea et al., "Aldosterone antagonism or synthase inhibition reduces end-organ damage induced by treatment with angiotensin and high salt," Kidney Int. 75(9):936-44 (2009).
Monticone et al., "Cardiovascular events and target organ damage in primary aldosteronism compared with essential hypertension: a systematic review and meta-analysis," Lancet Diabetes Endocrinol. 6(1):41-50 (2018).
Mulder et al., "Aldosterone synthase inhibition improves cardiovascular function and structure in rats with heart failure: a comparison with spironolactone," Eur Heart J. 29(17): 2171-2179 (2008).
Omata et al., "Cellular and Genetic Causes of Idiopathic Hyperaldosteronism," Hypertension 72(4):874-880 (2018).
Oshima et al., "Aldosterone is synthesized in and activates bulbospinal neurons through mineralocorticoid receptors and ENaCs in the RVLM," Hypertens Res. 36(6):504-512 (2013).
Rana et al., "Angiotensin II and aldosterone activate retinal microglia," Exp Eye Res 191:107902 (2020).
Rigel et al., "Pharmacodynamic and Pharmacokinetic Characterization of the Aldosterone Synthase Inhibitor FAD286 in Two Rodent Models of Hyperaldosteronism: Comparison with the 11ß-Hydroxylase Inhibitor Metyrapone," J Pharmacol Exp Ther. 334(1):232-243 (2010).
Shimoni et al., "Aldosterone and the autocrine modulation of potassium currents and oxidative stress in the diabetic rat heart," British Journal of Pharmacology 154(3):675-687 (2008).
Wang et al., "Role of brain aldosterone and mineralocorticoid receptors in aldosterone-salt hypertension in rats," Neuroscience 314:90-105 (2016).
Weldon et al., "Selectivity of BI 689648, a novel, highly selective aldosterone synthase inhibitor: comparison with FAD286 and LCI699 in nonhuman primates," Pharmacol Exp Ther. 359(1): 142-150 (2016).

\* cited by examiner

R-FADROZOLE FOR USE IN THE TREATMENT OF ALDOSTONERISM

The present invention relates to a composition for use in the treatment of a disease or disorder, wherein said disease or disorder is preferably a disease or disorder in which aldosterone overexposure contributes to the symptoms of said disease or disorder, said composition comprises a compound which is (R)-(+)-5-(p-cyanophenyl)-5,6,7,8-tetrahydroimidazo[1,5-a]pyridine or a pharmaceutically acceptable salt thereof, wherein preferably said compound is (R)-(+)-5-(p-cyanophenyl)-5,6,7,8-tetrahydroimidazolium [1,5-a]pyridine dihydrogen phosphate, and wherein said compound has an enantiomeric excess (ee) of the (R) form higher than or equal to 97%, and wherein said composition is administered once daily to a subject in need thereof. The invention further relates to a pharmaceutical composition comprising a daily dosage of said compound in a fixed-unit dosage form and to a combination comprising (i) said pharmaceutical composition or said compound; and (ii) instructions for administration of said pharmaceutical composition or said compound once per day.

RELATED ART

Aldosterone excess is associated with various harmful metabolic and cardiovascular structural effects, including sodium and water retention, hypokalemia, hypomagnesaemia, hypertension, left ventricular hypertrophy and cardiac fibrosis, and primary aldosteronism has a substantially adverse outcome when compared with essential hypertension. Accordingly, effective medical therapy both to lower blood pressure and antagonize the excess activation of the mineralocorticoid receptor are important therapeutic aims (Parthasarathy et al., 2011, J Hypertens 29: 980-990).

In the prior art, primary aldosteronism (PA) is defined as a group of disorders in which aldosterone production is inappropriately high for sodium status, relatively autonomous of the major regulators of secretion (angiotensin II, plasma potassium concentration), and non-suppressible by sodium loading. Such inappropriate production of aldosterone causes hypertension, cardiovascular damage, sodium retention, suppression of plasma renin, and increased potassium excretion that (if prolonged and severe) may lead to hypokalemia. PA is commonly caused by an adrenal adenoma, unilateral or bilateral adrenal hyperplasia (BAH), or in rare cases adrenal carcinoma or inherited conditions of familial hyperaldosteronism. PA is also known as Conn's syndrome (Funder et al., 2016, J Clin Endocrinol Metab 101: 1889-1916).

The capacity of adrenal glomerulosa cells to produce aldosterone is controlled largely by the regulated transcription of CYP11B2, the gene encoding aldosterone synthase. Aldosterone synthase inhibition has emerged as an option for the treatment of hypertension, heart failure and renal disorders, in addition to mineralocorticoid receptor (MR) blockade. The aim is to decrease aldosterone concentrations in both plasma and tissues, thereby decreasing MR-dependent and MR-independent effects in the cardiac, vascular and renal target organs. Since synthesis of aldosterone is closely linked to that of cortisol and aldosterone synthase is similar to 11-β-hydroxylase which catalysis the final step in cortisol synthesis, the search for highly selective CYP11B2 inhibitors has been complicated (Azizi et al., 2013, Nephrol Dial Transplant 28: 36-43).

Fadrozole hydrochloride (CGS16949A, INN: Fadrozole; U.S. Pat. Nos. 4,617,307; 4,728,645; 5,098,911; Trunet et al., 1992, J Clin Endocrinol Metab 74(3): 571-576), known as a non-steroidal aromatase inhibitor effective for advanced breast cancer treatment, has been found to only modestly affect basal plasma aldosterone levels without significantly elevating serum potassium when administered to healthy male subjects twice daily.

Subsequent preclinical studies demonstrated that the R-enantiomer of Fadrozole, (R)-(+)-5-(p-cyanophenyl)-5,6,7,8-tetrahydroimidazolium[1,5-a]pyridine chloride (CGS 20286, FAD 286A), is a potent inhibitor of CYP11B2 while the S-enantiomer is responsible for the strong and potent aromatase (CYP19) inhibiting activity of Fadrozole (J. Menard et al., J Hypertens (2006) 24:993; Fiebeler et al., Circulation (2005) 111:3078-94; Furet et al., J Med Chem (1993) 36:1393-1400; U.S. Pat. No. 5,057,521).

On the other hand, and despite its early discovery and further preclinical investigations (J. Menard et al., J Hypertens (2006) 24:993; Amar et al. (2010), Hypertension 56:831-838; U.S. Pat. Nos. 4,889,861; 5,057,521; Rigel et al., 2010, JPET 334(1):232-243), clinical development of (R)-(+)-5-(p-cyanophenyl)-5,6,7,8-tetrahydroimidazolium [1,5-a]pyridine chloride in humans has never been reported and neither a commercially viable synthesis for the R-enantiomer nor a satisfying chiral purity thereof has been disclosed.

In fact, the chiral purity of FAD 286A is considered to be of particular importance in light of the strong and potent aromatase inhibiting activity of the corresponding (S) enantiomer, since extensive evaluation of aromatase inhibitors in clinical trials has revealed numerous deleterious consequences of aromatase inhibition. For example, a systematic review and meta-analysis consisting of seven trials enrolling 30,023 postmenopausal women with breast cancer and treated with aromatase inhibitors revealed significant increases in the occurrence of bone fractures and cardiovascular disease (Amir et al., 2011, J Natl Cancer Inst 103: 1299-1309).

LCI699, an orally active aldosterone-synthase inhibitor similar in structure to FAD286 has been developed for human use and applied in a POC study in patients with primary aldosteronism, wherein LCI was administered to patients twice daily at a dose of each 0.5 mg (Amar et al., 2010, Hypertension 56:831-838). The twice-daily dosing scheme was selected based on the pharmacokinetic parameters of LCI699 observed in this phase I study (time to peak concentration of 1 hour and an elimination half-life of approximately 4 hours) and the high aldosterone levels expected in the patient with primary aldosteronism.

SUMMARY OF THE INVENTION

In a Phase I, placebo-controlled, safety, tolerability, pharmacodynamics, and pharmacokinetic study in healthy male patients, the inventors have surprisingly found that a very preferred compound of the present invention was able to effectively suppress plasma aldosterone levels in said patients compared to pretreatment values and placebo-treated control values. This finding is further in particularly remarkable since it was observed following administration once daily of the preferred compound as demonstrated in healthy male subjects within a single and multiple ascending dose study. Furthermore, the pharmacodynamic data surprisingly revealed that the preferred compound of the present invention dramatically suppressed plasma aldosterone concentrations over a 24 hour period at doses which did not adversely affect serum cortisol or reproductive hormone concentrations (LH, FSH, testosterone, estradiol). Moreover, it has been shown that said dramatic suppression of plasma aldosterone was obtained even while raising serum potassium levels a hallmark of potent aldosterone suppression.

Thus, and in particular, the inventors have developed a new dosing regimen for a composition comprising or consisting of a compound which is (R)-(+)-5-(p-cyanophenyl)-5,6,7,8-tetrahydroimidazo[1,5-a]pyridine or a pharmaceutically acceptable salt thereof, wherein preferably said compound is (R)-(+)-5-(p-cyanophenyl)-5,6,7,8-tetrahydroimidazolium[1,5-a]pyridine dihydrogen phosphate, wherein said compound has an enantiomeric excess (ee) of the (R) form of at least 97% for the treatment of diseases and disorders which aldosterone overexposure contributes to the symptoms of said diseases or disorders. When administered once daily, said composition effectively suppresses plasma aldosterone levels compared to pretreatment values and placebo-treated control values (Table 1). At all the time points at which aldosterone concentrations were measured, the once per day dose of said compound included in the composition of the invention significantly suppressed the concentrations compared to both pretreatment and placebo control values. Twenty-four hours after the last once daily dose of said compound of the invention, doses still suppressed plasma aldosterone by 32% and 50% compared to pretreatment values, respectively.

The once-daily dosing regimen is also supported by the pharmacokinetic data describing an elimination half-life for the compound of the invention as determined on day 1 and day 8 of dosing with the means for each dose ranging from a low 8.47 on day 1 at the 4 mg dose to 9.67 measured on day 8 at the 16 mg dose Table 5. Both the $C_{max}$ and $AUC_{0-\infty}$ for all dose levels were dose-proportional. The $T_{max}$ shows that the compound of the invention was absorbed rapidly at all dose levels and is comparable at day 1 and day 8. On Day 8, there was little accumulation of DP13 in plasma with a geometric mean accumulation ratio (RAObs) of 1.18 for $AUC_{0-tau}$ (Table 6).

The ability of said compound of the invention to provide therapeutic benefit with once-a-day dosing compared to multiple daily doses provides several benefits. In particular simplicity and convenience of the regimen and, as a consequence, improved patient compliance is highly desirable and of high medical benefit. Compliance is, thus, a particular advantage in the treatment of hypertensive disorders which exert no observable physical perceptions and therefore are more likely to suffer from deviations in compliance. In addition, multiple dosing is more likely to contribute to the increased experience of side-effects as a consequence of increased exposure to the maximal concentration of drug multiple times during the day. Following oral drug in-take the concentration of the drug in the circulation reaches a maximum ($C_{max}$) that is dependent on the extent and the rate of drug absorption and the disposition profile of the drug. Short term drug side-effects (gastric irritation, nausea, dizziness, increase heart rate, atrial fibrillation, hypotension etc.) are most likely to occur at or near the $C_{max}$; whereas, the therapeutic effect of drug with sustained duration of action usually occurs at concentrations slightly above the $C_{min}$. Therefore, it is advantageous to apply the compound of the invention with its effective aldosterone synthase activity only once daily and thus limit the peak drug exposure to the compound of the invention to once a day as opposed to multiple times.

The compound of the invention furthermore possess a very decreased and very low aromatase activity, beside the desired very high aldosterone synthase activity, which makes it possible to administer the compound of the invention only once a day in a single dose. The very low aromatase activity is of utmost importance with respect to the safety of the inventive compounds and compositions, and it is believed to be a prerequisite for clinical development and registered use as a medicament to treat diseases and disorders associated with aldosterone overexposure, in particular for premenopausal women, and thus women of child bearing potential, and pediatric patients. The latter is in particular true since and although the amount of aromatase and the percentage conversion of androgen to estrogen may be quantitatively small in extra-gonadal tissues, often being below 1% in any tissue, the effects in terms of hormonal action still may be great (Blakemore and Naftolin, Physiology (2016) 31:258-269). The typical need for life-time treatment of said diseases and disorders reinforces the advantages of the compound of the present invention in minimizing the contamination of the beneficial aldosterone synthase inhibiting (R)-(+)-5-(p-cyanophenyl)-5,6,7,8-tetrahydroimidazo[1,5-a]pyridine or a pharmaceutically acceptable salt thereof. Thus, the compound of the invention provide for the possibility of life-time medication with a high patient compliance for treatment of disorders negatively affected by aldosterone production due to minimizing the contamination and negative effects caused by the potent aromatase inhibiting (S)-enantiomer.

Accordingly, in a first aspect, the present invention provides for a composition for use in the treatment of a disease or disorder, said composition comprises a compound which is (R)-(+)-5-(p-cyanophenyl)-5,6,7,8-tetrahydroimidazo[1,5-a]pyridine of formula (I) or a pharmaceutically acceptable salt thereof, wherein said compound has an enantiomeric excess (ee) of the (R) form higher than or equal to 97%, and wherein said composition is administered once daily to a subject in need thereof.

(I)

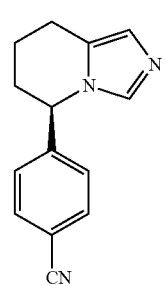

In a further aspect, the present invention provides for a composition for use in the treatment of a disease or disorder, wherein said disease or disorder is preferably primary aldosteronism or secondary aldosteronism, further preferably primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

In a further aspect, the present invention provides for a composition for use in the treatment of a disease or disorder, wherein said disease or disorder is a disease or disorder in which aldosterone overexposure contributes to the symptoms of said disease or disorder, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

In a further aspect, the present invention provides for composition for use in the treatment of a disease or disorder, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary aldosteronism or secondary aldosteronism, again further preferably said disease or disorder is primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

The inventors have found that (R)-(+)-5-(p-cyanophenyl)-5,6,7,8-tetrahydroimidazo[1,5-a]pyridine prepared by the process of the invention, pharmaceutically acceptable salt especially its phosphate salt or dihydrogen phosphate salt exhibit an unprecedented low inhibitory activity for aromatase. As demonstrated in Example 5, Tables 8-10, (R)-(+)-5-(p-cyanophenyl)-5,6,7,8-tetrahydroimidazo[1,5-a]pyridine inhibits aldosterone production (aldosterone synthase activity) and estradiol production (aromatase activity) by NCI-H295R adrenal cells with $IC_{50}$'s of 8.1 nM and 5760 nM, respectively; thus demonstrating a more than 700-fold greater inhibition of aldosterone synthase activity as compared to aromatase activity evidencing a highly beneficial safety profile for the inventive phosphate salt of (R)-(+)-5-(p-cyanophenyl)-5,6,7,8-tetrahydroimidazo[1,5-a]pyridine, and further the (R)-(+)-5-(p-cyanophenyl)-5,6,7,8-tetrahydroimidazolium[1,5-a]pyridine dihydrogen phosphate. Thus, the present invention is in particular suited for application in humans.

In a further aspect, the present invention provides for a pharmaceutical composition comprising a daily dosage of a compound in a fixed-unit dosage form, wherein said compound is (R)-(+)-5-(p-cyanophenyl)-5,6,7,8-tetrahydroimidazo[1,5-a]pyridine or a pharmaceutically acceptable salt thereof, and wherein said compound has an ee of the (R) form higher than or equal to 97%, wherein preferably said compound is (R)-(+)-5-(p-cyanophenyl)-5,6,7,8-tetrahydroimidazolium[1,5-a]pyridine dihydrogen phosphate.

In a further aspect, the present invention provides for a pharmaceutical composition for use in the treatment of a disease or disorder, wherein preferably said disease or disorder is primary aldosteronism or secondary aldosteronism, further preferably said disease or disorder is primary aldosteronism, and said pharmaceutical composition comprises a daily dosage of a compound in a fixed-unit dosage form, wherein said compound is (R)-(+)-5-(p-cyanophenyl)-5,6,7,8-tetrahydroimidazo[1,5-a]pyridine or a pharmaceutically acceptable salt thereof, and wherein said compound has an ee of the (R) form higher than or equal to 97%, wherein preferably said compound is (R)-(+)-5-(p-cyanophenyl)-5,6,7,8-tetrahydroimidazolium[1,5-a]pyridine dihydrogen phosphate.

In a further aspect, the present invention provides for a combination comprising
(i) the pharmaceutical composition according to the invention; or
a compound which is (R)-(+)-5-(p-cyanophenyl)-5,6,7,8-tetrahydroimidazo[1,5-a]pyridine or a pharmaceutically acceptable salt thereof, wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, and wherein preferably said compound is (R)-(+)-5-(p-cyanophenyl)-5,6,7,8-tetrahydroimidazolium[1,5-a]pyridine dihydrogen phosphate; and
(ii) instructions for administration of said pharmaceutical composition or said compound once per day. Preferably, said instructions for administration of said pharmaceutical composition or said compound are instructions of said pharmaceutical composition or said compound for use in a method to treat a disease or disorder being preferably primary aldosteronism or secondary aldosteronism, and further preferably being primary aldosteronism.

DETAILED DESCRIPTION OF THE INVENTION

Unless defined otherwise, all technical and scientific terms used herein have the same meanings as commonly understood by one of ordinary skill in the art to which this invention belongs.

The term "about" where used means especially ±10%, ±5% or ±3% (referring to the given numeric value, respectively), if not indicated otherwise. In each of the invention embodiments, "about" can be deleted. All ranges of values disclosed herein, should refer and include to any and all values falling within said range including the values defining the range. By way of clarification, for example, a value of 12 to 13 should refer to a value of 12 or 13 or any and all values falling within 12 and 13, and for example a daily dosage from 1 mg to 16 mg should refer to a daily dose of 1 mg or 16 mg or any and all values falling within 1 mg and 16 mg.

The term "chiral purity" as used herein is defined by the enantiomeric excess (ee) as determined by chiral HPLC (see Examples for details) and calculated by the equation:

$$ee = (A_R - A_S)/(A_R + A_S) \times 100\%,$$

wherein $A_R$ is the area of the (R)-(+)-5-(p-cyanophenyl)-5,6,7,8-tetrahydroimidazo[1,5-a]pyridine peak in the HPLC chromatogram of the sample solution and $A_S$ is the area of the (S)-(+)-5-(p-cyanophenyl)-5,6,7,8-tetrahydroimidazo[1,5-a]pyridine peak in the HPLC chromatogram of the sample solution.

The term "pharmaceutically acceptable salt" as used herein refers to a salt that is pharmaceutically acceptable and that possesses the desired pharmacological activity of the parent compound. Such salts include acid addition salts formed with inorganic acids or organic acids known to the skilled person in the art (P. Heinrich Stahl (Editor), Camille G. Wermuth (Editor); Handbook of Pharmaceutical Salts: Properties, Selection, and Use, 2nd Revised Edition, March 2011, Wiley-VCH, ISBN: 978-3-90639-051-2). Particularly preferred pharmaceutically acceptable salts in the present invention are acid addition salts, such as hydrochloride or phosphate salts, e.g. formed with phosphoric acid, i.e. a dihydrogen phosphate.

The term "phosphate salt" as used in the present application refers to compounds comprising (R)-(+)-5-(p-cyanophenyl)-5,6,7,8-tetrahydroimidazo[1,5-a]pyridine in its protonated form, i.e. the (R)-(+)-5-(p-cyanophenyl)-5,6,7,8-tetrahydroimidazolium[1,5-a]pyridine cation and further comprising anions derived from phosphoric acid, wherein said anions is typically and preferably dihydrogen phosphate $[H_2PO_4]^-$ or hydrogen phosphate $[HPO_4]^{2-}$. Preferably, the term "phosphate salt" as used in the present application refers to the dihydrogen phosphate of formula (I), that is, wherein the compound of formula (I) is protonated once and the counterion is $[H_2PO_4]^-$ and, thus, the stoichiometry of mono-protonated (R)-(+)-5-(p-cyanophenyl)-5,6,7,8-tetrahydroimidazo[1,5-a]pyridine to dihydrogen phosphate is 1:1. The latter compound is referred herein as (R)-(+)-5-(p-cyanophenyl)-5,6,7,8-tetrahydroimidazolium[1,5-a]pyridine dihydrogen phosphate.

The term "hydrochloride salt" or "chloride salt" as interchangeably used in the present application refers to compounds comprising (R)-(+)-5-(p-cyanophenyl)-5,6,7,8-tetrahydroimidazo[1,5-a]pyridine in its protonated form, i.e. the (R)-(+)-5-(p-cyanophenyl)-5,6,7,8-tetrahydroimidazolium[1,5-a]pyridine cation and further comprising chloride anions (Cl⁻).

The term "amorphous" as used herein, means a supercooled liquid or a viscous liquid which looks like a solid but does not have a regularly repeating arrangement of molecules that is maintained over a long range and does not have a melting point but rather softens or flows above its glass transition temperature.

The terms "crystalline" and "crystalline purity" as interchangeably used herein and related to the compounds of the invention, refer to a solid having a regularly repeating arrangement of molecules or external face planes. Preferably, the terms "crystalline" and "crystalline purity" when referring to (R)-(+)-5-(p-cyanophenyl)-5,6,7,8-tetrahydroimidazolium[1,5-a]pyridine dihydrogen phosphate comprising (R)-(+)-5-(p-cyanophenyl)-5,6,7,8-tetrahydroimidazolium[1,5-a]pyridine dihydrogen phosphate refers to the crystalline form I, wherein said crystalline form I is present of at least 60% by total weight, preferably of at least 70% by total weight, further preferably of at least 80% by total weight, again further preferably of at least 90% by total weight, and again further preferably of at least 95% by total weight. Further components may be, for example, amorphous (R)-(+)-5-(p-cyanophenyl)-5,6,7,8-tetrahydroimidazolium[1,5-a]pyridine dihydrogen phosphate. Crystalline purity may be determined by means of XRPD as described herein. Thus, in a preferred embodiment said XRPD can be determined using the following device, parameters and measuring conditions: Instrument: Bruker AXS D2 PHASER; Irradiation: CuKα (30 kV, 10 mA); scan range: 5 to 45° (2 theta value), sample rotation 5 rpm, 0.5 s/step, 0.010°/step, 3.0 mm detector slit.

The term "crystalline form I" as used herein refers to the (R)-(+)-5-(p-cyanophenyl)-5,6,7,8-tetrahydroimidazolium [1,5-a]pyridine dihydrogen phosphate, wherein said (R)-(+)-5-(p-cyanophenyl)-5,6,7,8-tetrahydroimidazolium[1,5-a] pyridine dihydrogen phosphate has an X-ray powder diffraction pattern comprising the following 2θ values measured using CuKα radiation: 19.504; 21.919 and 24.159, wherein each peak may vary by ±1 or preferably by ±0.5, or further preferably by ±0.2 degrees. In a preferred embodiment, "crystalline form I" as used herein refers to the (R)-(+)-5-(p-cyanophenyl)-5,6,7,8-tetrahydroimidazolium [1,5-a]pyridine dihydrogen phosphate, wherein said (R)-(+)-5-(p-cyanophenyl)-5,6,7,8-tetrahydroimidazolium[1,5-a] pyridine dihydrogen phosphate has an X-ray powder diffraction pattern comprising the following 2θ values measured using CuKα radiation, 19.504; 21.919 and 24.159, wherein each peak may vary by ±1 or preferably by ±0.5, or further preferably by ±0.2 degrees. In a further preferred embodiment, "crystalline form I" as used herein refers to the (R)-(+)-5-(p-cyanophenyl)-5,6,7,8-tetrahydroimidazolium [1,5-a]pyridine dihydrogen phosphate, wherein said (R)-(+)-5-(p-cyanophenyl)-5,6,7,8-tetrahydroimidazolium[1,5-a] pyridine dihydrogen phosphate has an X-ray powder diffraction pattern comprising the following 2θ values measured using CuKα radiation, 19.504; 21.919 and 24.159, wherein each peak may vary by ±0.5, or preferably by ±0.2 degrees. In again a further preferred embodiment, the term "crystalline form I" as used herein refers to the (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation, 19.504; 21.919 and 24.159, wherein each peak may vary by ±0.2 degrees. In another preferred embodiment, "crystalline form I" as used herein refers to the (R)-(+)-5-(p-cyanophenyl)-5,6,7,8-tetrahydroimidazolium [1,5-a]pyridine dihydrogen phosphate, wherein said (R)-(+)-5-(p-cyanophenyl)-5,6,7,8-tetrahydroimidazolium[1,5-a] pyridine dihydrogen phosphate has an X-ray powder diffraction pattern comprising the following 2θ values measured using CuKα radiation: 19.504; 21.919; 24.159; 16.003; 26.101; 27.168; 27.542 and 29.029, wherein each peak may vary by ±1 or preferably by ±0.5, or further preferably by ±0.2 degrees. In another preferred embodiment, "crystalline form I" as used herein refers to the (R)-(+)-5-(p-cyanophenyl)-5,6,7,8-tetrahydroimidazolium [1,5-a]pyridine dihydrogen phos-phate, wherein said (R)-(+)-5-(p-cyanophenyl)-5,6,7,8-tetrahydroimidazolium[1,5-a]pyridine dihydrogen phosphate has an X-ray powder diffraction pattern comprising the following 2θ values measured using CuKα radiation: 19.504; 21.919; 24.159; 16.003; 26.101; 27.168; 27.542 and 29.029, wherein each peak may vary by ±0.5, or preferably by ±0.2 degrees.

The term "anhydrous" as used herein refers to a crystalline form which contains less than 3%, preferably less than 2.5%, more preferably less than 2%, more preferably less than 1.5%, most preferably less than 1% water of hydration.

The term "non-hygroscopic" means the ability by the inventive pharmaceutically acceptable salts of (R)-(+)-5-(p-cyanophenyl)-5,6,7,8-tetrahydroimidazo[1,5-a]pyridine, and in particular of the phosphate salt of (R)-(+)-5-(p-cyanophenyl)-5,6,7,8-tetrahydroimidazo[1,5-a]pyridine, more preferably the (R)-(+)-5-(p-cyanophenyl)-5,6,7,8-tetrahydroimidazolium[1,5-a]pyridine dihydrogen phosphate, when they occur as powders or granules, to withstand exposure to the water vapor of an ambient atmosphere for 24 hours, weeks, months or years as a premise for commercial use without giving rise to adverse phenomena of aggregating, agglomerating, absorbing water, or deliquescing. Typically and preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 20-25° C. and a relative humidity of between 20% and 80%, preferably between 30% and 60%, it preserves its consistency as (preferably free-flowing) powder or granules over a period of at least one day, preferably one week, further preferably one month, again further preferably over a period of at least 3 months, and again further preferably for at least 6 months, and again further preferably or at least 1 year or more, in particular, to meet regulatory ICH standards. Further preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 20-25° C. and a relative humidity of between 20% and 80%, preferably between 30% and 60%, for a period of 24 hours, typically and preferably as determined in Example 5, it shows a weight increase of less than 5%, preferably of less than 3%, further preferably of less than 2%, again further preferably of less than 1%. Again further preferably, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at room temperature, most preferably at 20-25° C. and at a relative humidity of between 20% and 80%, preferably between 30% and 60%, for a period of 24 hours, typically and preferably as determined in Example 5, said phosphate salt, preferably said (R)-(+)-5-(p-cyanophenyl)-5,6,7,8-tetrahydroimidazolium[1,5-a]pyridine dihydrogen phosphate shows a water uptake of less than 5% (wt/wt), preferably of less than 3% (wt/wt), further preferably of less than 2% (wt/wt), again further preferably of less than 1% (wt/wt). Alternatively preferred, the term "non-hygroscopic" as used herein and referring to the phosphate salt of (R)-(+)-5-(p-cyanophenyl)-5,6,7,8-tetrahydroimidazo[1,5-a]pyridine, and preferably when referring to the (R)-(+)-5-(p-cyanophenyl)-5,6,7,8-tetrahydroimidazolium[1,5-a]pyridine dihydrogen phosphate, means that on storage in the open under normal ambient conditions, typically and preferably at 25° C. and a relative humidity of between of about 60%, for a period of 24 hours, preferably for a period of one month, further preferably for a period of at least 3 months, and again further preferably for at least 6 months, and again further preferably or at least 1 year, typically and preferably as determined in Example 9, the water content is less than 0.5 w/w %, preferably less than 0.4 w/w %, and further preferably equal or less than 0.3 w/w %.

As used herein, the term "specific optical rotation" refers to the specific optical rotation of a solution of the respective compound in a solvent, wherein said solvent is typically and preferably ethanol or CH$_3$CN:H$_2$O 1:1 (v/v), further preferably CH$_3$CN:H$_2$O 1:1 (v/v), and wherein said specific optical rotation is calculated by the formula: 100×α/(l×c), wherein α=observed rotation in degrees; l=cell path length in decimeters; c=concentration in grams per 100 ml, and wherein the measurement is performed at the sodium D line (i.e. 589.3 nm) at room temperature, typically and preferably at either 20° C. or 25° C. The term "specific optical rotation" is abbreviated as $[\alpha]_D^{20}$ or $[\alpha]_D^{25}$. Typically, for $[\alpha]_D^{20}$ or $[\alpha]_D^{25}$, either the sign of the rotation (+ or −) and its actual value is indicated herein or $[\alpha]_D^{20}$ or $[\alpha]_D^{25}$ is provided by way of its sign of the rotation (+ or −) and its actual value indicated in degrees (°). The complete unit as determined above (deg dm$^{-1}$ cm$^3$ g$^{-1}$) is typically omitted for the sake of clarity.

The term "solubility" as used herein refers to simplified descriptive solubilities (e.g. in water) in accordance with the U.S. Pharmacopoeia, Chapter "General Notices", § 5.30 "Description and Solubility" (and as defined below):

| Descriptive Term | Parts of Solvent Required for 1 Part of Solute |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble, or Insoluble | Greater than or equal to 10,000 |

The term "aromatase" refers to CYP19, a member of the cytochrome P450 superfamily, and is also known as estrogen synthase.

The term "aldosterone synthase" refers to the steroid hydroxylase cytochrome P450 enzyme CYP11B2.

The expression "IC$_{50}$" refers to the half maximal inhibitory concentration as commonly known in the art. The IC$_{50}$ for aromatase is determined by the cell-free human recombinant aromatase assay described in Example 5. The IC$_{50}$ for aldosterone synthase is determined by the human NCI-H295R cell assay described in Example 5.

The term "woman of childbearing potential" as used herein refers to a premenopausal female capable of becoming pregnant.

The term "pediatric patient" as used herein refers to a patient in the age category 0-18, preferably 0-16 years and include preterm and term newborn infants (0-27 days), infants and toddlers (28 days to 23 months), children (2-11 years) and adolescents (2 to 16/18 years).

When referring to "selectivity for aldosterone synthase over aromatase", the following ratio is meant:

$$\text{selectivity} = \frac{IC50 \text{ for aromatase}}{IC50 \text{ for aldosterone synthase}}$$

wherein both the IC$_{50}$ for aldosterone synthase and the IC$_{50}$ for aromatase are determined, preferably concomitantly, by the human NCI-H295R cell assay described in Example 5.

As outlined above, the phosphate salt of (R)-(+)-5-(p-cyanophenyl)-5,6,7,8-tetrahydroimidazo[1,5-a]pyridine, preferably the (R)-(+)-5-(p-cyanophenyl)-5,6,7,8-tetrahydroimidazolium[1,5-a]pyridine dihydrogen phosphate, inhibits aldosterone production (aldosterone synthase activity) and estradiol production (aromatase activity) by NCI-H295R adrenal cells with IC$_{50}$'s of 8.1 nM and 5760 nM, respectively (Example 5, Tables 8 and 9); thus demonstrating a selectivity of about 700 for aldosterone synthase over aromatase.

The term "disease" and "disorder" are used interchangeably herein, referring to any derangement or abnormal condition or function or morbid physical or mental state, especially an abnormal medical condition such as an illness or injury, wherein a tissue, an organ or an individual is not able to efficiently fulfil its function anymore. See Dorland's Illustrated Medical Dictionary (VSIB, Saunders Co., 27$^{th}$ ed., 1988). Typically, but not necessarily, a disease is associated with specific symptoms or signs indicating the presence of such disease. The presence of such symptoms or signs may thus, be indicative for a tissue, an organ or an individual suffering from a disease. Preferably, a tissue, an organ or an individual being at "risk of developing" shows potential of a disease emerging is also covered by the term "disease" or "disorder". Typically, the risk of developing a disease is associated with early or weak signs or symptoms of such disease.

As used herein, the expression "disease or disorder in which aldosterone overexposure contributes to the symptoms of said disease or disorder" preferably refers to a disease or disorder which is due to the abnormal or inappropriate activity/expression of aldosterone synthase and the biological activity or process which is associated with the abnormal or inappropriate expression of aldosterone synthase. Typical examples of diseases or disorders that are due to abnormal or inappropriate activity/expression of aldosterone synthase are primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction. Preferably said diseases or disorders that are due to abnormal or inappropriate activity/expression of aldosterone synthase are primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema.

The term "primary aldosteronism" (PA) is defined herein as a group of disorders characterized by an autonomous aldosterone excess leading to suppression of renin levels. An advocated screening test is the aldosterone-to-renin ratio with pathologically increased values in PA. PA thus covers also disorders in which aldosterone production is inappropriately high for sodium status, relatively autonomous of the major regulators of secretion (angiotensin II, plasma potassium concentration), and non-suppressible by sodium loading. The term "primary aldosteronism" covers also hyperaldosteronism and diseases and disorder which are a consequence of inappropriate production of aldosterone, which are typically and preferably selected from hypertension, cardiovascular damage, sodium retention, water retention, suppression of plasma renin, and increased potassium excretion and hypokalemia, hypomagnesaemia, left ventricular hypertrophy, cardiac fibrosis and kidney fibrosis, heart failure, arrhythmias, nephropathy, edema, and hypokalemia caused muscle weakness, cardiac fibrillation, weakened cardiac muscle contraction and cardiac failure. The term "primary aldosteronism" covers also diseases or disorders that cause PA, which are typically and preferably adrenal adenoma, unilateral and bilateral adrenal hyperplasia (BAH) (e.g. bilateral idiopathic (micronodular) adrenal hyperplasia and primary (unilateral) adrenal hyperplasia), adrenal carcinoma (e.g. aldosterone-producing adrenocortical carcinoma and ectopic aldosterone-producing adenoma or carcinoma), glucocorticoid-remediable aldosteronism, inherited conditions of familial aldosteronism and FH type II. PA is also known as Conn's syndrome. The excessive increase of aldosterone production in PA is a consequence of an escape of clusters of cells in the adrenal glomerulosa from the normal regulatory control of the aldosterone-renin-aldosterone.

The term "secondary aldosteronism" (SA) (also hyperreninism, or hyperreninemic hyperaldosteronism) as used herein refers to the hypersecretion of aldosterone secondary to stimulation from sources outside the adrenal gland. Extra-adrenal stimuli are for example renal hypoperfusion. SA is due to overactivity of the renin-angiotensin-aldosterone system. The term "secondary aldosteronism" covers diseases and disorder which are a consequence of inappropriate production of aldosterone and renin, which are typically and preferably selected from high plasma aldosterone levels, high plasma renin levels, hypertension, hypokalemic alkalosis that causes episodic weakness, paresthesias, transient paralysis, tetany; and peripheral edema. The term "secondary aldosteronism" also covers diseases or disorders that cause SA, such as reduced renal blood flow, obstructive renal artery disease (e.g., atheroma, stenosis), renal vasoconstriction, edematous disorders (e.g., heart failure, cirrhosis with ascites, nephrotic syndrome), a renin-producing tumor, a juxtaglomerular cell tumor, fibromuscular dysplasia, hyporeabsorption of sodium (as seen e.g. in Bartter and Gitelman syndromes), hypovolemia/hypotension. The term "secondary aldosteronism" covers also secondary hyperaldosteronism.

As used herein, the term "symptom" refers to any indication of an unusual state, disease or disorder and includes a departure from normal function or normal feeling which is either noticed by a subject, preferably patient, or objectively observable (effect or sign) reflecting the presence of the unusual state, disorder or disease.

As used herein, the term "day" or "daily" refers to either one calendar day or one 24-hour period, preferably the term "day" or "daily" refers to either one calendar day.

As used herein, the term "abnormal activity of aldosterone synthase" refers to an activity of aldosterone synthase which differs from the activity of the wild-type or native gene or protein, or which differs from the activity of the gene or protein in a healthy subject. The abnormal activity can be stronger or weaker than the normal activity.

As used herein, the term "inappropriate activity of aldosterone synthase" refers to the activity of aldosterone synthase of the wild-type or native gene or protein or to the activity of the gene or protein in a healthy subject, which is considered as appropriate in a healthy subject, but the same said activity is considered inappropriate for a diseased subject, i.e. said activity is too strong or too weak for a diseased subject.

The term "treating" and/or "treatment" as used herein refers to the management and care of a subject, preferably patient having a disease or disorder for which administration of one or more therapeutic compounds or compositions is indicated for the purpose of combating or alleviating symptoms and complications of those conditions. Treating includes administering one or more formulations of the present invention to prevent the onset of the symptoms or complications, alleviating the symptoms or complications, or eliminating the disease or disorder. As used herein, the term "treatment" (or "therapy" which are used interchangeably herein) refers to both therapeutic treatment and prophylactic or preventative measures. Preferably, "treatment" or "therapy" refers to therapeutic treatment.

The term "pharmaceutically acceptable excipient" as used herein includes any physiologically inert additive that is routinely used in pharmaceutical dosage forms. Pharmaceutically acceptable excipients are selected from the group comprising binders, diluents, carriers, lubricants, glidants, coating additives or combinations thereof. Additional suitable carriers for formulations of the active salts of the present invention can be found in Remington, The Science and Practice of Pharmacy, 2006, Lippincott Williams & Wilkins, Philadelphia.

As used herein, the term "subject" is used to mean an animal, preferably a mammal, including a human. Examples of mammals include humans, dogs, cows, horses, pigs, sheep, goats, cats. In a particularly preferred embodiment said subject is a human. The terms "patient" and "human", as used herein, are interchangeably used.

The term "administer" as used herein means to introduce or apply a therapeutic agent into or to the body of a subject, preferably patient in need thereof to treat a disease or condition.

The term "therapeutically effective amount" refers to a dosage of an active agent deemed to be effective to treat at least one sign or symptom of a disease or disorder or to provide a specific pharmacological response for which the active agent is administered. Amounts of an agent for administration may vary based upon the circumstances, e.g. diseased state of the subject, preferably patient, being treated, the dosage form, method of administration, subject factors, preferably patient factors and the like. A therapeutically effective amount of the active agent that is administered to a particular subject in a particular instance will not always be effective in treating the conditions described herein, even though such dosage is deemed to be a therapeutically effective amount by those of skill in the art.

The term "pharmaceutical composition" refers to a mixture containing at least one therapeutic agent to be administered to a subject, preferably a patient, in order to prevent or treat a particular disease or condition affecting the subject, preferably the patient.

In a first aspect, the present invention provides for a composition for use in the treatment of a disease or disorder, wherein said disease or disorder is preferably primary and secondary aldosteronism, said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, and wherein said composition is administered once per day (i.e. once daily) to a subject in need thereof.

Said compound according to the invention has an ee of the (R) form higher than or equal to 97%. In a preferred embodiment, said compound according to the invention has an ee of the (R) form higher than or equal to 98%, more preferably higher than or equal to 99%, and again more preferably higher than or equal to 99.5%, again more preferably higher than or equal to 99.8%, again more preferably higher than or equal to 99.9%. In a preferred embodiment, said compound according to the invention has an ee of the (R) form higher than or equal to 99.9%.

The present invention further provides a method for the treatment of a disease or disorder, preferably primary and secondary aldosteronism, said method comprises administering a composition once daily to a subject in need thereof, said composition comprises or consists of a therapeutically effective amount of a compound which is (R)-(+)-5-(p-cyanophenyl)-5,6,7,8-tetrahydroimidazo[1,5-a]pyridine or a pharmaceutically acceptable salt thereof, preferably a phosphate salt thereof or more preferably a dihydrogen phosphate salt thereof, wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%.

The present invention further relates to the use of a composition as a medicament, i.e. for the treatment of a disease or disorder, preferably primary and secondary aldosteronism, wherein said composition comprises or consists of a compound which is (R)-(+)-5-(p-cyanophenyl)-5,6,7,8-tetrahydroimidazo[1,5-a]pyridine or a pharmaceutically acceptable salt thereof, preferably a phosphate salt thereof, more preferably a or dihydrogen phosphate salt thereof; and wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%; and wherein said composition is administered once daily to a subject in need thereof.

The present invention further relates to the use of a composition for the manufacture of a medicament for the treatment of a disease or disorder, preferably primary and secondary aldosteronism, wherein said composition comprises or consists of a compound which is (R)-(+)-5-(p-cyanophenyl)-5,6,7,8-tetrahydroimidazo[1,5-a]pyridine or a pharmaceutically acceptable salt thereof, preferably a phosphate salt thereof, or more preferably the dihydrogen phosphate thereof; and wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%; and wherein said composition is administered once daily to a subject in need thereof.

The present invention further relates to the use of a composition according to the invention in the treatment of a disease or disorder, wherein said disease or disorder is preferably primary aldosteronism or secondary aldosteronism, further preferably primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

The present invention further relates to the use of a composition according to the invention in the treatment of a disease or disorder, wherein said disease or disorder is a disease or disorder in which aldosterone overexposure contributes to the symptoms of said disease or disorder, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

The present invention further relates to the use of a composition according to the invention in the treatment of a disease or disorder, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary aldosteronism or secondary aldosteronism, again further preferably said disease or disorder is primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

In a preferred embodiment, said composition for use according to the invention consist of a compound which is (R)-(+)-5-(p-cyanophenyl)-5,6,7,8-tetrahydroimidazo[1,5-a]pyridine or a pharmaceutically acceptable salt thereof, preferably a phosphate salt thereof, or more preferably the dihydrogen phosphate thereof.

In a preferred embodiment, said compound according to the invention is selected from the group consisting of (R)-(+)-5-(p-cyanophenyl)-5,6,7,8-tetrahydroimidazolium[1,5-a]pyridine, (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

In a preferred embodiment, said compound according to the invention is a pharmaceutically acceptable salt of (R)-(+)-5-(p-cyanophenyl)-5,6,7,8-tetrahydroimidazolium[1,5-a]pyridine. In a preferred embodiment, said compound according to the invention is selected from the group consisting of (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

Salts that are especially suited for rapid and high absorption of (R)-(+)-5-(p-cyanophenyl)-5,6,7,8-tetrahydroimidazolium[1,5-a]pyridine are the phosphate salt, more preferably the dihydrogen phosphate salt thereof. Once absorbed, lifetime (or half lifetime $T_{1/2}$) of the compound of the invention is independent of the salt but depends on the ee of the (R) form of (R)-(+)-5-(p-cyanophenyl)-5,6,7,8-tetrahydroimidazo[1,5-a]pyridine. In another preferred embodiment, said pharmaceutically acceptable salt is crystalline. In another preferred embodiment, said pharmaceutically acceptable salt is anhydrous. In another preferred embodiment, said pharmaceutically acceptable salt is non-hygroscopic. In another preferred embodiment, said pharmaceutically acceptable salt is non-hygroscopic and anhydrous. In another preferred embodiment, said pharmaceutically acceptable salt is non-hygroscopic and crystalline. In another preferred embodiment, said pharmaceutically acceptable salt is non-hygroscopic, anhydrous and crystalline.

In very preferred embodiment, said compound according to the invention is a phosphate salt of (R)-(+)-5-(p-cyanophenyl)-5,6,7,8-tetrahydroimidazolium[1,5-a]pyridine, more preferably a dihydrogen phosphate salt of (R)-(+)-5-(p-cyanophenyl)-5,6,7,8-tetrahydroimidazolium[1,5-a]pyridine. In another preferred embodiment, said compound is a dihydrogen phosphate salt of (R)-(+)-5-(p-cyanophenyl)-5,6,7,8-tetrahydroimidazolium[1,5-a]pyridine and said compound has an ee of the (R) form higher than or equal to 99%. In another preferred embodiment, said compound is a dihydrogen phosphate salt of (R)-(+)-5-(p-cyanophenyl)-5,6,7,8-tetrahydroimidazolium[1,5-a]pyridine and said compound has an ee of the (R) form higher than or equal to 99.9%.

Thus, in a very preferred embodiment, said compound is (R)-(+)-5-(p-cyanophenyl)-5,6,7,8-tetrahydroimidazolium[1,5-a]pyridine dihydrogen phosphate.

In a another preferred embodiment, said compound is crystalline (R)-(+)-5-(p-cyanophenyl)-5,6,7,8-tetrahydroimidazolium[1,5-a]pyridine dihydrogen phosphate. In another preferred embodiment, said compound is (R)-(+)-5-(p-cyanophenyl)-5,6,7,8-tetrahydroimidazolium[1,5-a]pyridine dihydrogen phosphate which is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

Said composition is administered once daily (q.d.) to a subject in need thereof. Preferably, said composition for use according to the invention is administered once within a period of about 24 h to the subject. In another preferred embodiment, said composition of the invention is administered once daily at the same time to the subject, e.g. once daily in the morning, at noon, in the evening or at night. In another preferred embodiment, the time period between two administrations of the composition of the invention is about 24 h.

The inventors discovered that said compound of the invention (unformulated or formulated in a composition) administered in oral doses of 1, 2, 4, 8, and 16 mg once daily effectively suppresses plasma aldosterone levels in normal men compared to pretreatment values and placebo-treated control values (Table 1 and 4). Responses of normal individuals to DP13 (which is (R)-(+)-5-(p-cyanophenyl)-5,6,7,8-tetrahydroimidazolium[1,5-a]pyridine dihydrogen phosphate as prepared according to Example 6) were evaluated and their plasma aldosterone and potassium responses were compared to each other and to placebo-treated individuals. At all the time points at which aldosterone concentrations were measured, the once daily dose of 8 mg and 16 mg significantly suppressed the concentrations compared to both pretreatment and placebo control values. Twenty-four hours after the last once daily dose of DP13 on day 8, the 8 mg and 16 mg doses had suppressed plasma aldosterone by 32% and 50% compared to pretreatment values, respectively. The 1 mg and 2 mg doses of DP13 suppressed plasma aldosterone by 52% and 61%, respectively. The 1 mg and 2 mg doses of DP13 suppressed plasma aldosterone by 52% and 61%, respectively, compared to placebo. 18 and 24 hours after the last once daily dose of DP13 on day 8, the 1 mg and 2 mg doses had suppressed plasma aldosterone by 18% and 39% compared to pretreatment values, respectively.

Thus, in a preferred embodiment, 24 h after administration of the once daily dose of the composition of the invention plasma aldosterone is suppressed at least by about 30%, preferably at least by about 50%, preferably at least by about 60% compared to pretreatment values, wherein preferably plasma aldosterone levels are measured as described in the phase I clinical study conducted by the Covance Clinical Research Unit Ltd. (see below Material & Methods); in particular, plasma samples are measured for aldosterone using the Liaison® chemiluminescent immunoassay kit supplied by DiaSorin S.p.A. Italy; the assays were performed according to the instructions provided by the manufacturer, and the analytical sensitivity was <0.97 ng/ml. Because this assay system uses specific monoclonal antibodies for aldosterone there are no cross reactions with other major potential reactants in the serum samples. The assay had a wide measuring range of 0.97-100 ng/ml and was designed for assessing aldosterone to diagnose and evaluate treatments for PA.

The once-daily dosing is supported by the pharmacokinetic data describing an elimination half-life for the compound of the invention as determined on day 1 and day 8 of dosing with the means for each dose ranging from a low 8.19 on day 1 for at the 1 mg dose or 8.47 on day 1 at the 4 mg dose to 9.67 measured on day 8 at the 16 mg dose (Table 5).

Thus, in a preferred embodiment, elimination half-life ($T_{1/2}$) of said compound of the invention is between about 8 h and about 11 h, more preferably between 8 h and 10 h. Preferably, elimination half-life ($T_{1/2}$) of said compound of the invention is measured in purified samples via mass spectrometry (LC-MS/MS)(Table 5). Said samples are preferably purified via liquid chromatography using a Waters, Acquity, UPLC with a Gemini 3 μm NX-C18, 5×2 mm column. The samples are prepared as described below under Materials & Methods, Pharmacokinetic Studies.

Both the $C_{max}$ and $AUC_{0-\infty}$ for all dose levels of DP13 and said compound of the invention were dose-proportional (Table 5). In a preferred embodiment, $C_{max}$ of said compound of the invention is from about 5 ng/ml, preferably from about 12 ng/ml, more preferably from about 14.0 ng/ml, again more preferably from about 30 ng/ml to about 77 ng/ml. In another more preferred embodiment, $C_{max}$ of said compound of the invention is from about 14 ng/ml to about 77 ng/ml. In another more preferred embodiment, $C_{max}$ of said compound of the invention is from about 14 ng/ml to about 67 ng/ml on the first day of administration or from about 15 ng/ml to about 77 ng/ml on the $8^{th}$ day of administration. Said $C_{max}$ values are preferably measured in purified samples via mass spectrometry (LC-MS/MS). Said samples are preferably purified via liquid chromatography using a Waters, Acquity, UPLC with a Gemini 3 μm NX-C18, 5×2 mm column. The samples are prepared as described below under Materials & Methods, Pharmacokinetic Studies.

$T_{max}$ shows that DP13 was absorbed rapidly at all dose levels and, $T_{max}$ is comparable at day 1 and day 8. On day 8, there was little accumulation of DP13 in plasma with a geometric mean accumulation ratio ($RA_{Obs}$) of 1.18 for $AUC_{0-tau}$ (individual range: 1.04 to 1.31).

In another preferred embodiment, $AUC_{0-\infty}$ of said compound of the invention is from about 167 ng·h/ml, preferably from about 335 ng·h/ml to about 725 ng·h/ml. $AUC_{0-t}$ is from 46 ng·h/ml, preferably from 133 ng·h/ml, more preferably from 139 ng·h/ml, again more preferably from about 281 ng·h/ml to about 725 ng·h/ml. Said $AUC_0$—, values are preferably measured in purified samples via mass spectrometry (LC-MS/MS). Said samples are preferably purified via liquid chromatography using a Waters, Acquity, UPLC with a Gemini 3 μm NX-C18, 5×2 mm column. The samples are prepared as described below under Materials & Methods, Pharmacokinetic Studies.

The once-daily dosing of the inventions also may prove more efficacy because of its limited production of 11β-deoxycorticosterone (DOC) as supported by the data of presented herein in Table 7. The compound of the invention raised DOC levels at all the doses both compared to placebo and pretreatment levels (Table 7). However, unlike with other Aldosterone synthase (CYP11B2) inhibitors, DOC increase induced by once daily administration of DP13 was rather low with the composition used according to the invention. LCI699 at doses of 0.5 and 1.0 mg taken twice a day decreased plasma aldosterone by 70-80% in PA patients, but increased DOC over 700% to a mean level of 9.8 ng/ml with individual levels ranging from 8.0 to 120.4 ng/ml at the 1.0 mg twice-daily dose (Amar et al., Hypertension (2010) 56:831). In contrast, the highest mean increase in DOC was only 0.52 ng/ml, nearly 20-fold less than seen with LCI699, and the highest individual value was 1.92 ng/ml, over 50-fold less than seen with LCI699 when using the composition according to the invention. The DOC concentrations observed when administering the composition according to the invention once daily are well below the critical range, 0.5 ng/ml to 0.7 ng/ml, expected to exert significant mineralocorticoid activity (Amar et al., Hypertension (2010) 56:831; Baxter et al., 1976, J. Clin. Invest. 58:579). Thus, in one embodiment, DOC concentrations induced by the composition used according to the invention are below 0.5 ng/ml. DOC is preferably quantified by an LC-MS/MS methodology. More preferably, in preparation the steroids are extracted using the Absolute/DQStereo17 Kit from Biocrates Life Sciences AG, Innsbruck, Austria; the steroids are extracted and subjected to LC-MS/MS analysis according to the manufacturer's instructions; the triple quadrupole mass spectrometer (Waters 1-Class 2D UPLC Xevo TQ-S is calibrated using the standards provided in the kit; the assays are performed as provided by the manufacturers.

The use of fadrozole as a treatment of aldosterone mediated disorders is untenable because of its effects on inhibiting aromatase activity which results in suppression of estrogens. The aromatase inhibition by fadrozole, which is the basis for its utility as a treatment for breast cancer, is evident from its suppression of estradiol and indirectly from its elevation of plasma testosterone and follicle stimulating hormone (FSH) concentrations as reported for healthy men (Bhatnagar et al., 1992, J. Steroid Biochem. Molec. Biol. 41(3-8):437-443). Unlike with fadrozole, DP13 neither inhibited estradiol nor increased circulating testosterone or FSH after once-daily oral dosing with 4, 8, or 16 mg. Estradiol was slightly increased at the 4 and 8 mg doses after 8 days of DP13 treatment. Thus, there is no evidence of estrogen suppression (aromatase inhibition) in normal healthy males treated with DP13.

Thus, in a preferred embodiment, said compound of the invention does not increase circulating testosterone or FSH after once-daily administration. Preferably said compound of the invention does not increase level of circulating testosterone or FSH after once-daily administration with daily oral doses of 4 mg, 8 mg, or 16 mg of the compound of the invention. In a further preferred embodiment, said compound of the invention does increase level of circulating estradiol. In a further preferred embodiment, said compound of the invention increases level of circulating estradiol by about 15% or more, preferably by about 17% or more, more preferably by about 25% or more, again more preferably by about 30% or more. Preferably, serum estradiol, testosterone, and follicle stimulating hormone (FSH) levels are measured by Covance's diagnostic unit, Harrogate, UK with the ADVIA Centaur®CP system (Siemens AG) having a sensitivity of 10 pg/ml. The ADVIA Centaur®CP FSH assay is a two-site sandwich immunoassay using direct chemiluminescence technology, which uses two antibodies that have specificity for the intact FSH molecule. The ADVIA Centaur®CP testosterone assay is a competitive, solid phase immunoassay using direct chemiluminescent technology. All of the above assays used for measuring serum estradiol, testosterone, and FSH levels were conducted as described by the manufacture.

In a preferred embodiment, said subject in need of the composition of the invention are mammals. More preferably said subject is a human. Preferably, said humans include women of child bearing potential and pediatric patients. In a preferred embodiment, said humans are women of child bearing potential and pediatric patients.

In a preferred embodiment, said subject in need of the composition of the invention is a human and said compound is a phosphate salt of (R)-(+)-5-(p-cyanophenyl)-5,6,7,8-tetrahydroimidazolium[1,5-a]pyridine, more preferably said compound is (R)-(+)-5-(p-cyanophenyl)-5,6,7,8-tetrahydroimidazolium[1,5-a]pyridine dihydro gen phosphate.

In a preferred embodiment, said composition of the invention is used for the treatment of a disease or disorder characterized by an aldosterone overexposure which contributes to the symptoms of said disease or disorder. More preferably, said disease or disorder is selected from the group consisting of primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy, cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction. In another preferred embodiment, said disease or disorder is selected from the group consisting of primary and secondary aldosteronism, sodium retention, water retention, hypokalemia, hypomagnesaemia, hypertension, left ventricular hypertrophy, cardiac fibrosis and kidney fibrosis. In another preferred embodiment, said disease or disorder is selected from the group consisting of primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy, cardiac fibrosis, cardiovascular damage, suppression of plasma renin, kidney fibrosis, arrhythmias, nephropathy, and edema. Again more preferably, said disease or disorder is primary and secondary aldosteronism. Most preferably said disease or disorder is primary aldosteronism.

It is believed that the excessive increase of aldosterone production in primary aldosteronism is a consequence of an escape of clusters of cells in the adrenal glomerulosa from the normal regulatory control of the aldosterone-renin-aldosterone. It is further believed thus that an aldosterone synthase inhibitor has the potential to prevent the sequalae of excessive aldosterone synthesis if provided at appropriate doses with appropriate duration of activity. In a preferred embodiment, said disease or disorder treated according to the invention is a condition following or occurring as a consequence of aldosterone overexposure.

In a preferred embodiment, said disease or disorder is primary and secondary aldosteronism, and said compound is a phosphate salt of (R)-(+)-5-(p-cyanophenyl)-5,6,7,8-tetrahydroimidazolium[1,5-a]pyridine, more preferably said compound is (R)-(+)-5-(p-cyanophenyl)-5,6,7,8-tetrahydroimidazolium[1,5-a]pyridine dihydrogen phosphate. In a preferred embodiment, said disease or disorder is primary and secondary aldosteronism, said subject is a human and said compound is a phosphate salt of (R)-(+)-5-(p-cyanophenyl)-5,6,7,8-tetrahydroimidazolium[1,5-a]pyridine, more preferably said compound is (R)-(+)-5-(p-cyanophenyl)-5,6,7,8-tetrahydroimidazolium[1,5-a]pyridine dihydrogen phosphate. Again more preferably, said (R)-(+)-5-(p-cyanophenyl)-5,6,7,8-tetrahydroimidazolium[1,5-a]pyridine dihydrogen phosphate of these embodiments is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

In a preferred embodiment, said composition for use according to the invention is administered once daily orally. In an also preferred embodiment, said composition for use according to the invention is formulated for oral administration (oral formulation). Said oral formulation is preferably solid. More preferably said oral formulation is selected from the group consisting of a tablet, pill, dispersible granule, cachet, capsule, powder, lozenge, suppository, and retention enema, most preferably of a tablet.

In a preferred embodiment, said composition for use according to the invention further comprises at least one pharmaceutically acceptable excipient.

In a preferred embodiment, said composition for use according to the invention is administered for a period of n consecutive days, wherein n is preferably >1. In a preferred embodiment, said composition for use according to the invention is administered once daily consecutively over a period of time. In a very preferred embodiment, said composition for use according to the invention is administered chronically. In another preferred embodiment, said composition for use according to the invention is administered for at least one month, preferably for at least two months, more preferably for at least three months, again more preferably for at least half a year, again more preferably for at least a one year, again more preferably for at least two years, again more preferably for at least 5 years, again more preferably for at least 10 years. In a very preferred embodiment said composition for use according to the invention is a life-time treatment.

In a preferred embodiment, said composition for use according to the invention comprises or preferably consists of a therapeutically effective once-per-day dosage of said compound of the invention, i.e. of the compound which is (R)-(+)-5-(p-cyanophenyl)-5,6,7,8-tetrahydroimidazo[1,5-a]pyridine or a pharmaceutically acceptable salt thereof, preferably a phosphate salt thereof or more preferably a dihydrogen phosphate thereof; and wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%.

In a preferred embodiment, said composition for use according to the invention is administered once daily in a dosage of 1 mg or more of said compound of the invention. In another preferred embodiment, said composition for use according to the invention is administered once daily in a dosage from 1 mg to 16 mg, preferably from 2 mg to 16 mg, more preferably from 4 mg to 16 mg, again more preferably from 8 mg to 16 mg, again more preferably from 12 mg to 16 mg of said compound of the invention. In a certain preferred embodiment, said composition for use according to the invention is administered once daily in a dosage from 1 mg to 16 mg of said compound of the invention. In another further preferred embodiment, said composition for use according to the invention is administered once daily in a dosage of 1, 2, 4, 8, 12, or 16 mg of said compound of the invention.

In a preferred embodiment, said composition for use according to the invention is orally administered once daily in a dosage of 1 mg or more of said compound of the invention. In a certain preferred embodiment, said composition for use according to the invention is orally administered once daily in a dosage from 1 mg to 16 mg of said compound of the invention.

In a preferred embodiment, said composition for use according to the invention is administered once daily in a dosage of 1 mg or more of said compound of the invention, wherein said compound is a phosphate salt of (R)-(+)-5-(p-cyanophenyl)-5,6,7,8-tetrahydroimidazolium[1,5-a]pyridine, preferably said compound is (R)-(+)-5-(p-cyanophenyl)-5,6,7,8-tetrahydroimidazolium[1,5-a]pyridine dihydrogen phosphate, and said disease or disorder is primary and secondary aldosteronism.

In a preferred embodiment, said composition for use according to the invention is administered once daily in a dosage of about 1 mg to about 16 mg of said compound of the invention, wherein said compound is a phosphate salt of (R)-(+)-5-(p-cyanophenyl)-5,6,7,8-tetrahydroimidazolium [1,5-a]pyridine, preferably said compound is (R)-(+)-5-(p-cyanophenyl)-5,6,7,8-tetrahydroimidazolium[1,5-a]pyridine dihydrogen phosphate, and said disease or disorder is primary and secondary aldosteronism. In a preferred embodiment, said composition for use according to the invention is administered once daily in a dosage of about 4 mg to about 16 mg of said compound of the invention, wherein said compound is a phosphate salt of (R)-(+)-5-(p-cyanophenyl)-5,6,7,8-tetrahydroimidazolium[1,5-a]pyridine, preferably said compound is (R)-(+)-5-(p-cyanophenyl)-5,6,7,8-tetrahydroimidazolium[1,5-a]pyridine dihydrogen phosphate, and said disease or disorder is primary and secondary aldosteronism. In a preferred embodiment, said composition for use according to the invention is administered once daily in a dosage of about 8 mg to about 16 mg of said compound of the invention, wherein said compound is a phosphate salt of (R)-(+)-5-(p-cyanophenyl)-5,6,7,8-tetrahydroimidazolium[1,5-a]pyridine, preferably said compound is (R)-(+)-5-(p-cyanophenyl)-5,6,7,8-tetrahydroimidazolium[1,5-a]pyridine dihydrogen phosphate, and said disease or disorder is primary and secondary aldosteronism. In a preferred embodiment, said composition for use according to the invention is administered once daily in a dosage of about 8 mg to about 16 mg of said compound of the invention, wherein said compound is a phosphate salt of (R)-(+)-5-(p-cyanophenyl)-5,6,7,8-tetrahydroimidazolium[1,5-a]pyridine, preferably said compound is (R)-(+)-5-(p-cyanophenyl)-5,6,7,8-tetrahydroimidazolium[1,5-a]pyridine dihydrogen phosphate, and said disease or disorder is primary and secondary aldosteronism. More preferably, said (R)-(+)-5-(p-cyanophenyl)-5,6,7,8-tetrahydroimidazolium[1,5-a]pyridine dihydrogen phosphate in these embodiments is crystalline, again more preferably said (R)-(+)-5-(p-cyanophenyl)-5,6,7,8-tetrahydroimidazolium[1,5-a] pyridine dihydrogen phosphate is a crystalline form I of (R)-(+)-5-(p-cyanophenyl)-5,6,7,8-tetrahydroimidazolium [1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

The oral dose of 4 mg/day of DP13 failed to lower the plasma aldosterone on day 9 twenty-four hours after the last of 8 daily doses. This failure is attributable to the significant increased plasma potassium levels apparent on day (08:00 h) pre-dose (Table 2). The plasma potassium increased in response to the decreased exchange of potassium for sodium by the kidney tubules resulting from the reduced aldosterone at earlier time points leading up to day 8, increases in circulating potassium stimulate aldosterone synthesis. The two higher doses of 8 and 16 mg are potent enough to maintain the suppression of plasma aldosterone even on day 9, 24 hours after the last dose on day 8 in the presents of the increased circulating potassium (Table 2). These data show that said compound of the invention can suppress aldosterone for long terms even at high potassium levels.

The failure of the 4 mg dose of DP13 to sustain the suppression of aldosterone throughout the dosing interval does not negate its potential benefits as an effective dose for treating primary aldosteronism (PA) for hypokalemia is a hallmark of PA and has serious potential consequences. Therefore, the increase in circulating potassium at the 4 mg dose could be of significant benefit to the PA patient population. In addition, primary aldosteronism is the most common cause of secondary hypertension, and excess of aldosterone in this clinical condition is considered to be responsible for hypokalemia and for blood pressure increase (Amar et al., 2010, op. cit.).

Moreover, when adrenocorticotropin (ACTH) was co-administered with the compound of the invention, oral doses of either 4, 8, or 16 mg of DP13 given once daily were able to prevent the increases in aldosterone elicited by ACTH in individuals only receiving daily doses of placebo (Table 3). For example, ACTH can be co-administered intravenously (i.v.) on day 7 of the treatment with the compound of the invention, two hours after the 08:00 h once daily dose of the compound of the invention. The placebo group's plasma aldosterone concentrations in response to ACTH ranged from 432 pmol/L to 825 pmol/L. These values are comparable to the range published for PA patients, 359 to 997 pmol/L (Amar et al., 2010, op. cit.). In addition, in the single-dose portion of this study, even a dose as low as 1 mg inhibited the ACTH-stimulated aldosterone response (Table 4).

In a preferred embodiment said composition for use according to the invention is administered in a once daily dosage from 1 mg to 16 mg, preferably from 2 mg to 16 mg, more preferably 4 mg to 16 mg, again more preferably 8 mg to 16 mg, again more preferably 12 mg to 16 mg, and wherein said disease or disorder is selected from the group consisting of primary and secondary aldosteronism and hypertension; and preferably said once daily dose is administered orally to a human. In a preferred embodiment said composition for use according to the invention is administered in a once daily dose from 8 mg to 16 mg, again more preferably from 12 mg to 16 mg, and wherein said disease or disorder is primary and secondary aldosteronism; and preferably said once daily dose is administered orally to a human. Preferably, said compound in these embodiments is (R)-(+)-5-(p-cyanophenyl)-5,6,7,8-tetrahydroimidazolium [1,5-a]pyridine dihydrogen phosphate.

In a preferred embodiment said pharmaceutically acceptable salt of (R)-(+)-5-(p-cyanophenyl)-5,6,7,8-tetrahydroimidazolium[1,5-a]pyridine for use according to the invention is a non-hygroscopic salt. More preferably said non-hygroscopic salt is a non-hygroscopic phosphate salt of (R)-(+)-5-(p-cyanophenyl)-5,6,7,8-tetrahydroimidazolium [1,5-a]pyridine, more preferably a non-hygroscopic dihydrogen phosphate salt of (R)-(+)-5-(p-cyanophenyl)-5,6,7,8-tetrahydroimidazolium[1,5-a]pyridine. Said phosphate salt and particularly said dihydrogen phosphate salt have been found to be non-hygroscopic and stable over an extended period of time, and hereby advantageous with respect to purity, water content and chiral purity. This is in particular important, since hygroscopicity typically affects negatively the stability of the active pharmaceutical ingredient.

Furthermore and importantly, the phosphate salt of (R)-(+)-5-(p-cyanophenyl)-5,6,7,8-tetrahydroimidazo[1,5-a]pyridine, and in particular (R)-(+)-5-(p-cyanophenyl)-5,6,7,8-tetrahydroimidazolium[1,5-a]pyridine dihydrogen phosphate for use according to the invention is crystalline in one stable form, typically and preferably in said crystalline form I. Unstable polymorphic forms typically affect negatively pharmaceutical efficacy properties.

In a preferred embodiment, said compound according to the invention is an anhydrous pharmaceutically acceptable salt of (R)-(+)-5-(p-cyanophenyl)-5,6,7,8-tetrahydroimidazolium[1,5-a]pyridine. More preferably said anhydrous pharmaceutically acceptable salt is an anhydrous phosphate salt, again more preferably an anhydrous dihydrogen phosphate salt of (R)-(+)-5-(p-cyanophenyl)-5,6,7,8-tetrahydroimidazolium[1,5-a]pyridine, for use according to the invention. The water uptake of the (R)-(+)-5-(p-cyanophenyl)-5,6,7,8-tetrahydroimidazolium[1,5-a]pyridine dihydrogen phosphate as measured by Dynamic Vapour Sorption studies is less than 1% at greater than 90% humidity and in addition the water uptake is reversible. Furthermore, the mass loss upon heating up to a temperature of 225° C. was only 1.4%. In conclusion, the phosphate salt, preferably the (R)-(+)-5-(p-cyanophenyl)-5,6,7,8-tetrahydroimidazolium[1,5-a]pyridine dihydrogen phosphate of the invention is not hygroscopic. As a consequence, the (R)-(+)-5-(p-cyanophenyl)-5,6,7,8-tetrahydroimidazolium[1,5-a]pyridine dihydrogen phosphate of the invention can be stored in bulk in customary pharmaceutical containment vessels at ambient conditions.

In a further preferred embodiment, said compound according to the invention is a crystalline pharmaceutically acceptable salt of (R)-(+)-5-(p-cyanophenyl)-5,6,7,8-tetrahydroimidazolium[1,5-a]pyridine, preferably a crystalline phosphate salt and more preferably a crystalline dihydrogen phosphate salt of (R)-(+)-5-(p-cyanophenyl)-5,6,7,8-tetrahydroimidazolium[1,5-a]pyridine. A phosphate salt and especially the dihydrogen phosphate salt of (R)-(+)-5-(p-cyanophenyl)-5,6,7,8-tetrahydroimidazolium[1,5-a]pyridine according to the invention has been found to be highly crystalline and having a high level of crystalline purity. Furthermore, the phosphate salt and especially the dihydrogen phosphate salt of (R)-(+)-5-(p-cyanophenyl)-5,6,7,8-tetrahydroimidazolium[1,5-a]pyridine dihydrogen phosphate according to the invention with the described exceptional chiral purity is present in one single crystalline form with a defined x-ray structure and R-(+)-absolute configuration on carbon 5, its chiral center. Polymorphism is a serious concern when seeking to provide safe and efficacious forms of a drug. Despite this, the inventors have discovered that the crystalline form I of (R)-(+)-5-(p-cyanophenyl)-5,6,7,8-tetrahydroimidazolium[1,5-a]pyridine dihydrogen phosphate is physically stable, i.e. polymorphism was not observed and can be obtained predictably and reliably (Example 6, step 4). Furthermore, XRPD analysis of (R)-(+)-5-(p-cyanophenyl)-5,6,7,8-tetrahydroimidazolium[1,5-a]pyridine dihydrogen phosphate showed that the substance was essentially free of amorphous material (i.e. amorphous material was not detectable). XRPD was performed, if not described otherwise, as described in the Examples section.

In a further preferred embodiment, said compound according to the invention is an anhydrous crystalline pharmaceutically acceptable salt of (R)-(+)-5-(p-cyanophenyl)-5,6,7,8-tetrahydroimidazolium[1,5-a]pyridine. More preferably said anhydrous crystalline pharmaceutically acceptable salt is an anhydrous crystalline phosphate salt, again more preferably an anhydrous crystalline dihydrogen phosphate salt of (R)-(+)-5-(p-cyanophenyl)-5,6,7,8-tetrahydroimidazolium[1,5-a]pyridine, for use according to the invention.

In one embodiment, the compound according to the invention is a crystalline form I of (R)-(+)-5-(p-cyanophenyl)-5,6,7,8-tetrahydroimidazolium[1,5-a]pyridine dihydrogen phosphate, said crystalline form I is characterized by an X-ray powder diffraction pattern comprising the following 2θ values measured as described in the Examples section: 19.504; 21.919 and 24.159. In one embodiment there is provided a crystalline form I of (R)-(+)-5-(p-cyanophenyl)-5,6,7,8-tetrahydroimidazolium[1,5-a]pyridine dihydrogen phosphate for use according to the invention, said crystalline form I is characterized by an X-ray powder diffraction pattern comprising the following 2θ values measured as described in the Examples section: 19.504; 21.919 and 24.159, wherein each peak may vary by ±1 or preferably by ±0.5, or further preferably by ±0.2 degrees. In a preferred embodiment, said X-ray powder diffraction pattern further comprises the following 2θ values: 16.003; 26.101; 27.168; 27.542 and 29.029. In a preferred embodiment, said X-ray powder diffraction pattern further comprises the following 2θ values: 16.003; 26.101; 27.168; 27.542 and 29.029, wherein each peak may vary by ±1 or preferably by ±0.5, or further preferably by ±0.2 degrees. In a particularly preferred embodiment, there is provided a crystalline form I of (R)-(+)-5-(p-cyanophenyl)-5,6,7,8-tetrahydroimidazolium[1,5-a]pyridine dihydrogen phosphate for use according to the invention, said crystalline form I is characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165; 27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464. In another particularly preferred embodiment, there is provided a crystalline form I of (R)-(+)-5-(p-cyanophenyl)-5,6,7,8-tetrahydroimidazolium[1,5-a]pyridine dihydrogen phosphate for use according to the invention, said crystalline form I is characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165;

27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464, wherein each peak may vary by ±1 or preferably by ±0.5, or further preferably by ±0.2 degrees. In another particularly preferred embodiment, there is provided a crystalline form I of (R)-(+)-5-(p-cyanophenyl)-5,6,7,8-tetrahydroimidazolium[1,5-a]pyridine dihydrogen phosphate, characterized by an X-ray powder diffraction pattern comprising at least one, more preferably 2, 3, 4, 5, 6, 7, 8, 9, 10, 11, 12, 13, 14, 15, 16 or all of the following 2θ values: 6.023129; 9.969034; 11.26224; 11.22848; 11.96566; 12.77761; 13.79347; 14.39314; 15.3394; 16.00317; 16.27337; 17.07502; 17.27593; 17.9904; 18.38238; 18.65471; 18.96096; 19.14281; 19.504; 20.01265; 20.58808; 20.43302; 20.72112; 21.12683; 21.91906; 22.59202; 24.44788; 24.15917; 24.48119; 25.70071; 26.10094; 26.58127; 27.16767; 27.54165; 27.71408; 28.27603; 28.09725; 28.54909; 29.02939; 29.71314; 30.07578; 30.68808; 30.92867; 31.6379; 32.27005; 32.79806; 33.20638; 33.23304; 33.65808; 34.41793; 34.35512; 35.02142; 35.06671; 35.68978; 35.93622; 36.50305; 36.56591; 36.92023; 37.14021; 39.60815; 37.89624 and 40.22464, wherein each peak may vary by ±0.5, or preferably by ±0.2 degrees. In one embodiment, the three largest peaks of crystalline form I in the XRPD diffractogram have a relative intensity of 1 to 0.85 to 0.55, especially of 1 to 0.9 to 0.6, more especially of 1 to 0.95 to 0.65, e.g. of 1 to 0.97 to 0.68 (obtainable by integration of each of the peaks in the XRPD diagrams). In a particular embodiment the largest peak is at a 2-theta (θ) value of about 21.919 and the second-largest peak is at a 2-theta (θ) value of about 19.504 and the third-largest peak is at a 2-theta (θ) value of about 24.159, respectively. In a further particular embodiment the largest peak is at a 2-theta (θ) value of about 21.919±0.5, or preferably by ±0.2 degrees, and the second-largest peak is at a 2-theta (θ) value of about 19.504±0.5, or preferably by ±0.2 degrees and the third-largest peak is at a 2-theta (θ) value of about 24.159±0.5, or preferably by ±0.2 degrees, respectively.

It was further found that (R)-(+)-5-(p-cyanophenyl)-5,6,7,8-tetrahydroimidazolium[1,5-a]pyridine dihydrogen phosphate (crystalline form I) has a single sharp and high melting point of 189° C. as measured by DSC, again indicating high physical stability and which is further very beneficial with regards to drug manufacture, storage and processing to pharmaceutical formulations. Accordingly, in one embodiment, there is provided (R)-(+)-5-(p-cyanophenyl)-5,6,7,8-tetrahydroimidazolium[1,5-a]pyridine dihydrogen phosphate having a melting point of equal or between 184° C. to 193° C. for use according to the invention, and wherein preferably said (R)-(+)-5-(p-cyanophenyl)-5,6,7,8-tetrahydroimidazolium[1,5-a]pyridine dihydrogen phosphate has a melting point of equal or between 188° C. to 190° C., typically and preferably using thermogravimetric analysis/differential scanning calorimetry (TGA/DSC). In a further embodiment, there is provided (R)-(+)-5-(p-cyanophenyl)-5,6,7,8-tetrahydroimidazolium[1,5-a]pyridine dihydrogen phosphate having a melting point of 184° C., 185° C., 186° C., 187° C., 188° C., 189° C., 190° C., 191° C., 192° C., 193° C. or 194° C. for use according to the invention, most preferably 189° C. In a further embodiment, the compound according to the invention is (R)-(+)-5-(p-cyanophenyl)-5,6,7,8-tetrahydroimidazolium[1,5-a]pyridine dihydrogen phosphate having a melting point of 189±5° C., 189±2° C., 189±1° C. or 189±0.5° C. The melting temperatures herein, if not described otherwise, are obtained by TGA/DSC as described in the Examples section.

The (R)-(+)-5-(p-cyanophenyl)-5,6,7,8-tetrahydroimidazolium[1,5-a]pyridine dihydrogen phosphate prepared from the enantiomerically pure (R)-(+)-5-(p-cyanophenyl)-5,6,7,8-tetrahydroimidazo[1,5-a]pyridine free base described herein and thus having an ee of >99.9%, was found to have a specific optical rotation ($[\alpha]_D^{20}$) of +98.1° ($CH_3CN:H_2O$ 1:1 (v/v); Example 6). Accordingly, in one very preferred embodiment of the present invention, the compound according to the invention is (R)-(+)-5-(p-cyanophenyl)-5,6,7,8-tetrahydroimidazolium[1,5-a]pyridine dihydrogen phosphate having a specific optical rotation ($[\alpha]D^{20}$) ($CH_3CN:H_2O$ 1:1 (v/v)) of at least +94°, preferably of at least +95°, further preferably of at least +96°, more preferably of at least +97°, even more preferably of at least +98°. In a further embodiment, said compound according to the invention is (R)-(+)-5-(p-cyanophenyl)-5,6,7,8-tetrahydroimidazo[1,5-a]pyridine having a specific optical rotation $[\alpha]_D^{25}$ (ethanol) of at least +120°, preferably of at least +121°, further preferably of at least +122°, again further preferably of at least +123°, again further preferably of at least +124°, again further preferably of at least +125°, again further preferably of at least +126°, and again further preferably of at least +127°. In another embodiment, said compound according to the invention is a chloride salt of (R)-(+)-5-(p-cyanophenyl)-5,6,7,8-tetrahydroimidazolium[1,5-a]pyridine having a specific optical rotation $[\alpha]_D^{20}$ (ethanol) of at least +95°, preferably of at least +96°, further preferably of at least +97°, more preferably of at least +98°, even more preferably of at least +99°, further preferably of at least +100°, more preferably of at least +101°, even more preferably of at least +102°, and again more preferably of at least +103°, even more preferably of at least +104°, for use according to the invention.

In one embodiment, the compound according to the invention is from (R)-(+)-5-(p-cyanophenyl)-5,6,7,8-tetrahydroimidazo[1,5-a]pyridine of formula (I) or a pharmaceutically acceptable salt thereof, in particular (R)-(+)-5-(p-cyanophenyl)-5,6,7,8-tetrahydroimidazolium[1,5-a]pyridine dihydrogen phosphate, wherein said compound has a solubility in water of more than 50% vol/vol.

The inventors have surprisingly found that (R)-(+)-5-(p-cyanophenyl)-5,6,7,8-tetrahydroimidazo[1,5-a]pyridine prepared by the process of the invention (Example 6), as well as its phosphate salt, preferably the (R)-(+)-5-(p-cyanophenyl)-5,6,7,8-tetrahydro-imidazolium[1,5-a]pyridine dihydrogen phosphate, exhibit an unprecedented low inhibitory activity for aromatase (Example 5), which is crucial to avoid side effects related to inhibition of aromatase when using the compounds of the invention in methods of treating diseases or disorders related to enhanced aldosterone synthase activity and/or enhanced levels of aldosterone, in particular when used for women of child bearing potential and pediatric patients.

Thus, in a preferred embodiment, said compound according to the invention is (R)-(+)-5-(p-cyanophenyl)-5,6,7,8-tetrahydroimidazo[1,5-a]pyridine or a pharmaceutically acceptable salt thereof, preferably the phosphate salt thereof, further preferably the (R)-(+)-5-(p-cyanophenyl)-5,6,7,8-tetrahydroimidazolium[1,5-a]pyridine dihydrogen phosphate, wherein said compound inhibits aromatase activity in the cell-free human recombinant aromatase enzyme assay described in Example 5 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or at least 1650 nM. In a more preferred embodiment, said compound according to the invention inhibits aromatase activity in the cell-free human recombinant aromatase enzyme assay described in Example 5 with an $IC_{50}$ of 700 nM or more, preferably 1000 nM or more, and more preferably 1500 nM or more; and wherein further preferably said compound is (R)-(+)-5-(p-cyanophenyl)-5,6,7,8-tetrahydroimidazolium[1,5-a]pyridine dihydrogen phosphate.

In a further preferred embodiment, said compound according to the invention is (R)-(+)-5-(p-cyanophenyl)-5,6,7,8-tetrahydroimidazo[1,5-a]pyridine or a pharmaceutically acceptable salt thereof, preferably the phosphate salt thereof, further preferably the (R)-(+)-5-(p-cyanophenyl)-5,6,7,8-tetrahydroimidazolium[1,5-a]pyridine dihydrogen phosphate, wherein said compounds of the invention inhibit aldosterone synthase in the NCI-H295R adrenal cell assay described in Example 5 with an $IC_{50}$ of 100 nM or less. In one embodiment, the compounds of the invention inhibit aldosterone synthase in the NCI-H295R adrenal cell assay described in Example 5 with an $IC_{50}$ of 90 nM or less, 80 nM or less, 70 nM or less, 60 nM or less, 50 nM or less, 40 nM or less, 35 nM or less, 30 nM or less, 25 nM or less, or 20 nM or less; in particular 15 nM or less, e.g., 15 nM, 14 nM, 13 nM, 12 nM, 11 nM, 10 nM, 9 nM, 8 nM, 7 nM, 6 nM, 5 nM, 4 nM, 3 nM, 2 nM or 1 nM or less. In a preferred embodiment, the compounds of the invention inhibit aldosterone synthase in the NCI-H295R adrenal cell assay described in Example 5 with an $IC_{50}$ of 10 nM or less. In a more preferred embodiment, said compound according to the invention inhibit aldosterone synthase in the NCI-H295R adrenal cell assay described in Example 5 with an $IC_{50}$ of 100 nM or less, preferably 50 nM or less, and more preferably 10 nM or less; and wherein further preferably said compound is (R)-(+)-5-(p-cyanophenyl)-5,6,7,8-tetrahydroimidazolium[1,5-a]pyridine dihydrogen phosphate.

In a further preferred embodiment, said compound according to the invention is (R)-(+)-5-(p-cyanophenyl)-5,6,7,8-tetrahydroimidazo[1,5-a]pyridine or a pharmaceutically acceptable salt thereof, preferably the phosphate salt thereof, further preferably the (R)-(+)-5-(p-cyanophenyl)-5,6,7,8-tetrahydroimidazolium[1,5-a]pyridine dihydrogen phosphate, wherein said compound of the invention has a selectivity for aldosterone synthase over aromatase of 30 or more, preferably 50 or more, more preferably 100 or more, more preferably 150 or more, more preferably 200 or more, more preferably 250 or more, more preferably 300 or more, more preferably 350 or more, more preferably 400 or more, more preferably 450 or more, more preferably 500 or more, more preferably 550 or more, more preferably 600 or more, more preferably 650 or more, most preferably 700 or more, wherein said selectivity is determined by the ratio of the $IC_{50}$ values for inhibition of aromatase and aldosterone synthase; and wherein the $IC_{50}$ values for inhibition of aldosterone synthase and aromatase are both measured, preferably concomitantly, in the NCI-H295R adrenal cell assay described in Example 5. In a more preferred embodiment, said compound according to the invention has a selectivity for aldosterone synthase over aromatase of 50 or more, preferably 100 or more, most preferably 700 or more; wherein said selectivity is determined by the ratio of the $IC_{50}$ values for inhibition of aromatase and aldosterone synthase; wherein the $IC_{50}$ values for inhibition of aldosterone synthase and aromatase are both measured, preferably concomitantly, in the NCI-H295R adrenal cell assay described in Example 5; and wherein further preferably said compound is (R)-(+)-5-(p-cyanophenyl)-5,6,7,8-tetrahydroimidazolium[1,5-a]pyridine dihydrogen phosphate.

In a further very preferred embodiment, the compound according to the invention is crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, for use in a method of treating a disease or disorder in a human, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary and secondary aldosteronism, wherein preferably said human is a woman of child bearing potential or a pediatric patient, and wherein said (R)-(+)-5-(p-cyanophenyl)-5,6,7,8-tetrahydroimidazolium[1,5-a]pyridine dihydrogen phosphate inhibits aromatase activity in the cell-free human recombinant aromatase enzyme assay described in Example 5 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or at least 1650 nM.

In a further very preferred embodiment, the compound according to the invention is crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, for use in a method of treating a disease or disorder in a human, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary and secondary aldosteronism, wherein preferably said human is a woman of child bearing potential or a pediatric patient, said compound according to the invention has a selectivity for aldosterone synthase over aromatase of 50 or more, preferably 100 or more, most preferably 700 or more; wherein said selectivity is determined by the ratio of the IC50 values for inhibition of aromatase and aldosterone synthase; wherein the IC50 values for inhibition of aldosterone synthase and aromatase are both measured, preferably concomitantly, in the NCI-H295R adrenal cell assay described in Example 5.

In a further very preferred embodiment, the compound according to the invention is crystalline (R)-(+)-5-(p-cyanophenyl)-5,6,7,8-tetrahydroimidazolium[1,5-a]pyridine dihydrogen phosphate, preferably anhydrous crystalline (R)-(+)-5-(p-cyanophenyl)-5,6,7,8-tetrahydroimidazolium[1,5-a]pyridine dihydrogen phosphate, having an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, for use in a method of treating a disease or disorder in a human, wherein said disease or disorder is selected from primary and primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary and secondary aldosteronism, wherein preferably said human is a woman of child bearing potential or a pediatric patient, and said compound according to the invention inhibits aldosterone synthase in the NCI-H295R adrenal cell assay described in Example 5 with an $IC_{50}$ of 100 nM or less, preferably 50 nM or less, and more preferably 10 nM or less.

In a preferred embodiment said composition for use according to the invention is administered in a once daily dosage from 1 mg to 16 mg, preferably from 2 mg to 16 mg, more preferably 4 mg to 16 mg, again more preferably 8 mg to 16 mg, again more preferably 12 mg to 16 mg, and wherein said disease or disorder is selected from the group consisting of primary and secondary aldosteronism and hypertension; and preferably said once daily dose is administered orally to a human, and said compound according to the invention inhibits aldosterone synthase in the NCI-H295R adrenal cell assay described in Example 5 with an $IC_{50}$ of 100 nM or less, preferably 50 nM or less, and more preferably 10 nM or less.

In a further aspect, the invention provides for a pharmaceutical composition comprising a daily dosage of said compound of the invention in a fixed-unit dosage form, wherein said compound of the invention is (R)-(+)-5-(p-cyanophenyl)-5,6,7,8-tetrahydroimidazo[1,5-a]pyridine or a pharmaceutically acceptable salt thereof, and wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%. Thus, said once daily dosage of the compound of the invention which is the active ingredient is present in the pharmaceutical composition in a single a fixed-unit dosage form.

Preferably said pharmaceutical composition of the invention is a daily fixed-unit dosage form. Said daily fixed-unit dosage form comprises the compound of the invention in an amount of a fixed daily dose.

In a preferred embodiment, said compound according to the invention is selected from the group consisting of (R)-(+)-5-(p-cyanophenyl)-5,6,7,8-tetrahydroimidazolium[1,5-a]pyridine, (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

In a preferred embodiment, said compound according to the invention is a pharmaceutically acceptable salt of (R)-(+)-5-(p-cyanophenyl)-5,6,7,8-tetrahydroimidazolium[1,5-a]pyridine. In a preferred embodiment, said compound according to the invention is selected from the group consisting of (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

In another preferred embodiment, said pharmaceutically acceptable salt is crystalline. In another preferred embodiment, said pharmaceutically acceptable salt is anhydrous. In another preferred embodiment, said pharmaceutically acceptable salt is non-hygroscopic. In another preferred embodiment, said pharmaceutically acceptable salt is non-hygroscopic and anhydrous. In another preferred embodiment, said pharmaceutically acceptable salt is non-hygroscopic and crystalline. In another preferred embodiment, said pharmaceutically acceptable salt is non-hygroscopic, anhydrous and crystalline.

In very preferred embodiment, said compound according to the invention is a phosphate salt of (R)-(+)-5-(p-cyanophenyl)-5,6,7,8-tetrahydroimidazolium[1,5-a]pyridine, more preferably a dihydrogen phosphate salt of (R)-(+)-5-(p-cyanophenyl)-5,6,7,8-tetrahydroimidazolium[1,5-a]pyridine. In another preferred embodiment, said compound is a dihydrogen phosphate salt of (R)-(+)-5-(p-cyanophenyl)-5,6,7,8-tetrahydroimidazolium[1,5-a]pyridine and said compound has an ee of the (R) form higher than or equal to 99%. In another preferred embodiment, said compound is a dihydrogen phosphate salt of (R)-(+)-5-(p-cyanophenyl)-5,6,7,8-tetrahydroimidazolium[1,5-a]pyridine and said compound has an ee of the (R) form higher than or equal to 99.9%.

Thus, in a very preferred embodiment, said compound is (R)-(+)-5-(p-cyanophenyl)-5,6,7,8-tetrahydroimidazolium[1,5-a]pyridine dihydrogen phosphate.

In a another preferred embodiment, said compound is crystalline (R)-(+)-5-(p-cyanophenyl)-5,6,7,8-tetrahydroimidazolium[1,5-a]pyridine dihydrogen phosphate. In another preferred embodiment, said compound is (R)-(+)-5-(p-cyanophenyl)-5,6,7,8-tetrahydroimidazolium[1,5-a]pyridine dihydrogen phosphate which is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

In one embodiment, said pharmaceutical composition is formulated for oral administration. Said oral formulation is preferably solid. More preferably said oral formulation is selected from the group consisting of a tablet, pill, dispersible granule, cachet, capsule, powder, lozenge, suppository, and retention enemas.

In one embodiment, said pharmaceutical composition is an oral unit dose forms. In a further embodiment, said pharmaceutical composition is an oral solid unit dose forms e.g. tablets and capsules etc. . . .

In a preferred embodiment, said pharmaceutical composition comprises the compound of the invention in a daily dosage of 1 mg or more. In another preferred embodiment, said pharmaceutical composition comprises the compound of the invention in a daily dosage from 1 mg to 16 mg, more preferably from 2 mg to 16 mg, again more preferably from 4 mg to 16 mg, again more preferably from 8 mg to 16 mg, again more preferably from 12 mg to 16 mg. In a certain preferred embodiment, said pharmaceutical composition comprises the compound of the invention in a daily dosage from 1 mg to 16 mg of said compound of the invention. In another further preferred embodiment, said pharmaceutical composition comprises the compound of the invention in a daily dosage of 1, 2, 4, 8, 12, or 16 mg.

In a preferred embodiment, said pharmaceutical composition is formulated for oral administration and comprises the compound of the invention in a daily dosage of 1 mg or more of said compound of the invention. In a certain preferred embodiment, said pharmaceutical composition is formulated for oral administration and comprises the compound of the invention in a daily dosage from 1 mg to 16 mg.

In a further aspect, the invention provides for a combination comprising (i) the pharmaceutical composition according to the invention or a compound which is (R)-(+)-5-(p-cyanophenyl)-5,6,7,8-tetrahydroimidazo[1,5-a]pyridine or a pharmaceutically acceptable salt thereof; and (ii) instructions for administration of said pharmaceutical composition or said compound once per day, wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%.

In a preferred embodiment, said compound according to the invention is selected from the group consisting of (R)-(+)-5-(p-cyanophenyl)-5,6,7,8-tetrahydroimidazolium [1,5-a]pyridine, (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydro gen phosphate, and (R)-(+)-5-(p-cyanophenyl)-5,6,7,8-tetrahydroimidazo[1,5-a]pyridine hydrogen phosphate.

In a preferred embodiment, said compound according to the invention is a pharmaceutically acceptable salt of (R)-(+)-5-(p-cyanophenyl)-5,6,7,8-tetrahydroimidazolium[1,5-a]pyridine. In a preferred embodiment, said compound according to the invention is selected from the group consisting of (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

In another preferred embodiment, said compound according to the invention is a phosphate salt of (R)-(+)-5-(p-cyanophenyl)-5,6,7,8-tetrahydroimidazolium[1,5-a]pyridine, more preferably a dihydrogen phosphate salt of (R)-(+)-5-(p-cyanophenyl)-5,6,7,8-tetrahydroimidazolium[1,5-a]pyridine.

More preferably said pharmaceutical composition of the invention comprises a daily dosage of the compound of the invention in a fixed-unit dosage form. More preferably said pharmaceutical composition of the invention is a daily fixed-unit dosage form.

In a further aspect, the present invention provides for a process for preparing a compound which is (R)-(+)-5-(p-cyanophenyl)-5,6,7,8-tetrahydroimidazo[1,5-a]pyridine or a pharmaceutically acceptable salt thereof, and wherein very preferably said pharmaceutically acceptable salt is the phosphate salt thereof, and further preferably the (R)-(+)-5-(p-cyanophenyl)-5,6,7,8-tetrahydroimidazolium[1,5-a]pyridine dihydrogen phosphate. The inventive processes comprise the steps of: (i) reacting racemic 5-(p-cyanophenyl)-5,6,7,8-tetrahydroimidazo[1,5-a]pyridine with a (−)-O,O'-acylated L-tartaric acid, in particular (−)-O,O'-dibenzoyl-L-tartaric acid to form the diastereomeric (R)-(+)-5-(p-cyanophenyl)-5,6,7,8-tetrahydroimidazo[1,5-a]pyridine dibenzoyl-L-tartrate salt; and (ii) recrystallizing at least once the tartrate salt obtained in step i; and (iii) liberating the free base (R)-(+)-5-(p-cyanophenyl)-5,6,7,8-tetrahydroimidazo[1,5-a]pyridine by adding a base to a solution of said tartrate salt obtained in step ii; and optionally (iv) forming a pharmaceutically acceptable salt by reacting said free base with an acid, preferably with phosphoric acid (H3PO4). In one embodiment, said (i) reacting racemic 5-(p-cyanophenyl)-5,6,7,8-tetrahydroimidazo[1,5-a]pyridine with a (−)-O,O'-acylated L-tartaric acid, in particular (−)-O,O'-dibenzoyl-L-tartaric acid to form the diastereomeric (R)-(+)-5-(p-cyanophenyl)-5,6,7,8-tetrahydroimidazo[1,5-a]pyridine dibenzoyl-L-tartrate salt is effected in an alcoholic solution, preferably in a solution of ethanol, at a temperature of below about 50° C., preferably of below about 45° C., and further preferably of below about 40° C. In one embodiment, said (ii) recrystallizing at least once the tartrate salt obtained in step (i) is effected in an aqueous-alcoholic solution, preferably in an aqueous ethanol solution, wherein preferably the ratio of water:ethanol is of about 2.4:about 10.

In one embodiment, the process of the invention for preparing a compound which is (R)-(+)-5-(p-cyanophenyl)-5,6,7,8-tetrahydroimidazo[1,5-a]pyridine or a pharmaceutically acceptable salt thereof does not comprise a step of chiral resolution of 5-(p-cyanophenyl)-5,6,7,8-tetrahydroimidazo[1,5-a]pyridine (fadrozole) by means of chiral preparative HPLC, wherein preferably said process for preparing a compound which is (R)-(+)-5-(p-cyanophenyl)-5,6,7,8-tetrahydroimidazo[1,5-a]pyridine or a pharmaceutically acceptable salt thereof of the invention does not comprise a step of chiral resolution of 5-(p-cyanophenyl)-5,6,7,8-tetrahydroimidazo[1,5-a]pyridine (fadrozole) by means of chiral HPLC. Such step of chiral resolution by means of chiral HPLC can typically comprise (i) repetitive chiral HPLCs on low capacity columns or (ii) preparative HPLC on high capacity column.

In a preferred embodiment, the process of the invention yields (R)-(+)-5-(p-cyanophenyl)-5,6,7,8-tetrahydroimidazo[1,5-a]pyridine and its pharmaceutically acceptable salts thereof, in particular the phosphate salt thereof, further preferably the (R)-(+)-5-(p-cyanophenyl)-5,6,7,8-tetrahydroimidazolium[1,5-a]pyridine dihydrogen phosphate, with an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to again more preferably higher than or equal to again more preferably higher than or equal to 99.9%.

In a further preferred embodiment, the process of the invention yields (R)-(+)-5-(p-cyanophenyl)-5,6,7,8-tetrahydroimidazo[1,5-a]pyridine and its pharmaceutically acceptable salts thereof, in particular the phosphate salt thereof, further preferably (R)-(+)-5-(p-cyanophenyl)-5,6,7,8-tetrahydroimidazolium[1,5-a]pyridine dihydrogen phosphate, wherein said (R)-(+)-5-(p-cyanophenyl)-5,6,7,8-tetrahydroimidazo[1,5-a]pyridine and its pharmaceutically acceptable salts thereof inhibit aromatase activity in the cell-free human recombinant aromatase enzyme assay described in Example 5 with an $IC_{50}$ of 700 nM or more, preferably 750 nM or more, more preferably 800 nM or more, more preferably 850 nM or more, more preferably 900 nM or more, more preferably 950 nM or more, more preferably 1000 nM or more, more preferably 1050 nM or more, more preferably 1100 nM or more, more preferably 1150 nM or more, more preferably 1200 nM or more, more preferably 1250 nM or more, more preferably 1300 nM or more, more preferably 1350 nM or more, more preferably 1400 nM or more, more preferably 1450 nM or more, more preferably 1500 nM or more, more preferably 1550 nM or more, most preferably at least 1600 nM, e.g. 1610 nM or 1620 nM or 1630 nM or 1640 nM or 1650 nM or more.

The inventive processes, thus, utilize crystallization to obtain (R)-(+)-5-(p-cyanophenyl)-5,6,7,8-tetrahydroimidazo[1,5-a]pyridine and its pharmaceutically acceptable salts thereof, and very preferably its phosphate salt thereof, and again further the (R)-(+)-5-(p-cyanophenyl)-5,6,7,8-tetrahydroimidazolium[1,5-a]pyridine dihydrogen phosphate, in exceptional high chiral purity for commercial pharmaceutical use. On a commercial scale, crystallization is much more advantageous being more economical than chromatographic resolution by allowing for larger batch preparation, less expensive equipment and facilities, and not requiring specialized expertise.

Further preferred aspects and embodiments of the invention are as follows:

1. A composition for use in the treatment of a disease or disorder, wherein said disease or disorder is preferably primary aldosteronism or secondary aldosteronism, further preferably primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

2. A composition for use in the treatment of a disease or disorder, wherein said disease or disorder is a disease or disorder in which aldosterone overexposure contributes to the symptoms of said disease or disorder, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

3. A composition for use in the treatment of a disease or disorder, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary aldosteronism or secondary aldosteronism, again further preferably said disease or disorder is primary aldosteronism, wherein said composition is administered once daily to a subject in need thereof and said composition comprises a compound which is (R)-(+)-5-(p-cyanophenyl)-5,6,7,8-tetrahydroimidazo[1,5-a]pyridine or a pharmaceutically acceptable salt thereof, wherein said compound has an enantiomeric excess (ee) of the (R) form higher than or equal to 97%.

4. The composition for use according to any one of the preceding embodiments, wherein said compound is selected from (R)-(+)-5-(p-cyanophenyl)-5,6,7,8-tetrahydroimidazolium[1,5-a]pyridine, (R)-(+)-5-(p-cyanophenyl)-5,6,7,8-tetrahydroimidazo[1,5-a]pyridine hydrochloride, (R)-(+)-5-(p-cyanophenyl)-5,6,7,8-tetrahydroimidazolium[1,5-a]pyridine dihydrogen phosphate, and (R)-(+)-5-(p-cyanophenyl)-5,6,7,8-tetrahydroimidazo[1,5-a]pyridine hydrogen phosphate.

5. The composition for use according to any one of the preceding embodiments, wherein said compound is (R)-(+)-5-(p-cyanophenyl)-5,6,7,8-tetrahydroimidazolium[1,5-a]pyridine dihydrogen phosphate.

6. The composition for use according to any one of the preceding embodiments, wherein said pharmaceutically acceptable salt is crystalline.

7. The composition for use according to any one of the preceding embodiments, wherein said pharmaceutically acceptable salt is anhydrous.

8. The composition for use according to any one of the preceding embodiments, wherein said pharmaceutically acceptable salt is non-hygroscopic.

9. The composition for use according to any one of embodiments 5 to 8, wherein said (R)-(+)-5-(p-cyanophenyl)-5,6,7,8-tetrahydroimidazolium[1,5-a]pyridine dihydrogen phosphate has a melting point of equal or between 184° C. to 193° C., and wherein preferably said (R)-(+)-5-(p-cyanophenyl)-5,6,7,8-tetrahydroimidazolium[1,5-a]pyridine dihydrogen phosphate has a melting point of equal or between 188° C. to 190° C. as determined by thermogravimetric analysis/differential scanning calorimetry (TGA/DSC).

10. The composition for use according to any one of embodiments 5 to 9, wherein said (R)-(+)-5-(p-cyanophenyl)-5,6,7,8-tetrahydroimidazolium[1,5-a]pyridine dihydrogen phos-phate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5, or preferably by ±0.2 degrees.

11. The composition for use according to any one of the preceding embodiments, wherein said compound inhibits aromatase activity in the cell-free human recombinant aromatase enzyme assay with an $IC_{50}$ of 700 nM or more, preferably 1000 nM or more, and more preferably 1500 nM or more.

12. The composition for use according to any of the preceding embodiments, wherein said compound inhibits aldosterone synthase in the NCI-H295R adrenal cell assay with an $IC_{50}$ of 100 nM or less, preferably 50 nM or less, and more preferably 10 nM or less.

13. The composition for use according to any of the preceding embodiments, wherein said compound has a selectivity for aldosterone synthase over aromatase of 50 or more, preferably of 100 or more, most preferably of 700 or more; wherein said selectivity is determined by the ratio of the $IC_{50}$ values for inhibition of aromatase and aldosterone synthase; wherein the $IC_{50}$ values for inhibition of aldosterone synthase and aromatase are both measured in the NCI-H295R adrenal cell assay.

14. The composition for use according to any of the preceding embodiments, wherein elimination half-life ($T_{1/2}$) of said compound is longer than 8 h, preferably elimination half-life ($T_{1/2}$) of said compound is between 8 h and 11 h, further preferably elimination half-life ($T_{1/2}$) of said compound is between about 8 h and about 10 h, preferably measured by mass spectrometry (LC-MS/MS).

15. The composition for use according to any of the preceding embodiments, wherein $C_{max}$ of said compound is from about 5 ng/ml to about 90 ng/ml, preferably from about 10 ng/ml to about 80 ng/ml, further preferably from about 14 ng/ml to about 77 ng/ml, preferably measured by mass spectrometry (LC-MS/MS).

16. The composition for use according to any of the preceding embodiments, wherein said subject is a human.

17. The composition for use according to any of the preceding embodiments, wherein said subject is a woman of childbearing potential or a pediatric patient.

18. The composition for use according to any of the preceding embodiments in the treatment of a disease or disorder which aldosterone overexposure contributes to the symptoms of said diseases or disorders.

19. The composition for use according to any of the preceding embodiments, wherein said disease or disorder is selected from primary aldosteronism, secondary aldosteronism, heart failure, chronic renal failure, hypertension, restenosis, obesity, nephropathy, post-myocardial infarction, renal fibrosis, coronary heart disease, sodium retention, water retention, hypokalemia, hypomagnesaemia, hypertension, left ventricular hypertrophy and cardiac fibrosis, cardiovascular damage, suppression of plasma renin, kidney fibrosis, arrhythmias, nephropathy, edema, and hypokalemia caused muscle weakness, cardiac fibrillation and weakened cardiac muscle contraction, preferably said disease or disorder is primary aldosteronism or secondary aldosteronism, again further preferably said disease or disorder is primary aldosteronism.

20. The composition for use according to any of the preceding embodiments, wherein said composition is administered orally.

21. The composition for use according to any of the preceding embodiments, wherein said composition is administered once daily in a dosage of 1 mg or more of said compound, preferably via oral administration.

22. The composition for use according to any of the preceding embodiments, wherein said composition is administered once daily in a dosage from 1 mg to 16 mg, preferably from 2 mg to 16 mg, more preferably 4 mg to 16 mg, again more preferably 8 mg to 16 mg, again more preferably 12 mg to 16 mg of said compound.

23. The composition for use according to any of the preceding embodiments, wherein said disease or disorder is preferably primary aldosteronism, further preferably primary aldosteronism in a human, wherein said treatment decreases the level of aldosterone in plasma, as compared when no such treatment is effected.

24. The composition for use according to any of the preceding embodiments, wherein said disease or disorder is preferably primary aldosteronism, further preferably primary aldosteronism in a human, wherein said treatment decreases the level of aldosterone in plasma by at least 20%, preferably 25%, again further preferably by at least 30% for a period of at least 18 hours, preferably of about 24 hours, after said once daily administration, as compared when no such treatment is effected.

25. The composition for use according to any of the preceding embodiments, wherein said disease or disorder is preferably primary aldosteronism, further preferably primary aldosteronism in a human, wherein said treatment decreases the level of aldosterone in plasma by at least about 20%, preferably by at least about 25%, more preferably by at least about 30%, again more preferably by at least about 50%, for a period of at least 18 hours, preferably of 24 hours, after said once daily administration, as compared to pretreatment values.

26. A pharmaceutical composition comprising a daily dosage of a compound in a fixed-unit dosage form, wherein said compound is (R)-(+)-5-(p-cyanophenyl)-5,6,7,8-tetrahydroimidazo[1,5-a]pyridine or a pharmaceutically acceptable salt thereof, and wherein said compound has an ee of the (R) form higher than or equal to 97%, wherein preferably said compound is (R)-(+)-5-(p-cyanophenyl)-5,6,7,8-tetrahydroimidazolium[1,5-a]pyridine dihydrogen phosphate.

27. The pharmaceutical composition according to embodiments 26 formulated for oral administration.

28. The pharmaceutical composition according to embodiments 26 or 27, wherein said daily dosage is 1 mg or more, preferably from 1 mg to 16 mg, further preferably from 2 mg to 16 mg, more preferably 4 mg to 16 mg, again more preferably 8 mg to 16 mg, again more preferably 12 mg to 16 mg.

29. The pharmaceutical composition according to embodiments 26 or 27, wherein said daily dosage is 1 mg, 2 mg, 4 mg, 8 mg, 12 mg or 16 mg, preferably said daily dosage is 4 mg, 8 mg, 12 mg or 16 mg.

30. The pharmaceutical composition according to any one of the embodiments 26 to 29, wherein said pharmaceutical composition is in the form of tablets, pills, dispersible granules, cachets, capsules, powders, lozenges, suppositories or retention enemas, wherein preferably said pharmaceutical composition is in the form of a tablet.

31. A combination comprising
(i) the pharmaceutical composition according to the embodiments 26-30; or
   a compound which is (R)-(+)-5-(p-cyanophenyl)-5,6,7,8-tetrahydroimidazo[1,5-a]pyridine or a pharmaceutically acceptable salt thereof, wherein said compound has an ee of the (R) form higher than or equal to 97%, preferably higher than or equal to 98%, more preferably higher than or equal to 99%, and again more preferably higher than or equal to 99.5%, again more preferably higher than or equal to 99.8%, again more preferably higher than or equal to 99.9%, and wherein preferably said compound is (R)-(+)-5-(p-cyanophenyl)-5,6,7,8-tetrahydroimidazolium[1,5-a]pyridine dihydrogen phosphate; and
(ii) instructions for administration of said pharmaceutical composition or said compound once per day.

EXAMPLES

Equipment, Materials and Methods
Administration of DP13
The DP13 data presented herein were collected in a Phase I, double blind, placebo-controlled, single and multiple ascending doses, safety, tolerability, pharmacodynamics, and pharmacokinetic study of DP13 in healthy male subjects conducted by the Covance Clinical Research Unit Ltd., Leeds, UK.

In the single dose portion of the study individuals received 1, 2, 4, 8, 12, or 16 mg of DP13 at 08:00 h on day 1. There were 6 subjects treated with each dose and twelve subjects treated with placebo (two placebo-treated-subjects included with each dose group). In the multiple dose portion of the study thirty-two individuals were studied in 3 groups with 8 subjects per dose of DP13 and the remaining 8 subjects receiving a placebo. The subjects received a daily oral dose of either 4, 8, or 16 mg of DP13 or placebo daily for 8 days in the fasted state at 08:00 h.

In both the multiple and single-dose portions of the study the participants were required to follow a sodium/potassium diet beginning 5 days before the first oral treatment with either DP13 or placebo. The diet consisted of 70-80 mEq/day of sodium and 80-90 mEq/day of potassium. Blood samples were obtained daily at the time points indicated in the accompanying Tables for measurements of aldosterone, 11β-deoxycorticosterone (DOC), and potassium ($K^+$). All of the blood samples were obtained while the subjects were seated in a resting state.

For a stress test, on day 1 of the single dose phase of the study or on day 7 of the multiple dose phase of the study an ACTH (Synacten) stress test was initiated as follows. One and one-half hours after the daily dose of DP13 or placebo on day 1 or 7, a blood sample was withdrawn (baseline for response to Synacten) and one-half hour later an intravenous dose of Synacten (250 μg) was administered. Blood samples were obtained 60 min post-Synacten. The samples were analyzed for aldosterone and 11β-deoxycorticosterone (DOC) by the Clinical Chemistry Unit at the University Hospital Inselspital Bern, Bern Switzerland. Aldosterone was measured using the Liaison® chemiluminescent immunoassay kit supplied by DiaSorin S.p.A. Italy. Because this assay system uses specific monoclonal antibodies for aldosterone there are no cross reactions with other major potential reactants in the serum samples. The assays were performed according to the instructions provided by the manufacturer. The assay had a wide measuring range of 0.97-100 ng/ml and was designed for assessing aldosterone to diagnose and evaluate treatments for PA. The analytical sensitivity was <0.97 ng/ml.

DOC was quantified by an LC-MS/MS methodology. In preparation the steroids were extracted using the Absolute/DQStereo17 Kit from Biocrates Life Sciences AG, Innsbruck, Austria. The steroids were extracted and subjected to LC-MS/MS analysis according to the manufacturer's instructions. The triple quadrupole mass spectrometer (Waters 1-Class 2D UPLC Xevo TQ-S was calibrated using the standards provided in the kit. The assays were performed as provided by the manufacturers.

Serum cortisol, estradiol, testosterone, and follicle stimulating hormone (FSH) were measured by Covance's diagnostic unit, Harrogate, UK with the ADVIA Centaur®CP system (Siemens AG). The ADVIA Centaur®CP cortisol assay is a competitive double antibody, solid phase immunoassay using chemiluminescent technology for detection and has an analytical sensitivity of 0.20 μg/dL. The ADVIA Centaur enhanced estradiol assay is a fully automated, monoclonal competitive, chemiluminescent immunoassay, and has a sensitivity of 10 pg/ml. The ADVIA Centaur®CP FSH assay is a two-site sandwich immunoassay using direct chemiluminescence technology, which uses two antibodies that have specificity for the intact FSH molecule. The ADVIA Centaur®CP testosterone assay is a competitive, solid phase immunoassay using direct chemiluminescent technology. All of the above assays were conducted as described by the manufacture.

Statistical evaluations of the hormonal responses was performed using the two-tailed, paired Student's t-test to evaluate within treatment group data, and data from between treatment groups utilized the two-tailed t-test equal variance model.

Pharmacokinetic Studies

For the pharmacokinetic studies and data mentioned above, especially in Example 3, blood samples were obtained on day 1 pre-dose and 0.5, 1, 1.5, 2, 3, 4, 6, 8, 12, and 16 hours post-dose, and on days 2-7 pre-dose, and on day 8 at 0.5, 1, 1.5, 2, 3, 4, 6, 8, 12, 16, and 24 hours post-dose. The DP13 was measured by a procedure developed by the Covance Clinical Pharmacokinetic Unit as follows. The blood samples were collected in K2EDTA, centrifuged and the plasma stored at −80° C. The samples were prepared for analysis by liquid/liquid extraction as follows. A 50 μL aliquot was extracted with 25 μL of methanol:water (50:50) and mixed; following which 250 μL of ammonia acetate 100 mM:ammonia hydroxide (95:5) was added and the solution was mixed. 750 μL of ethyl acetate was then added and mixed by aspirating and centrifuged at approximately 2500×g for 5 min. 400 μL of the organic layer was collected and evaporated under nitrogen at 40° C. The dried sample was reconstituted in 200 μL of ammonia acetate 10 mM:methanol:ammonia hydroxide (70:30:0.35) and centrifuged at 2000×g for 5 min. at room temperature. The extracted sample was then subjected to liquid chromatography using a Waters, Acquity, UPLC with a Gemini 3 μm NX-C18, 5×2 mm column. An injection volume of 8 μL was analyzed using Mobil phase A consisting of ammonium acetate 10 mM:ammonium hydroxide (100:0.5) and Mobile phase B consisting of methanol. The purified sample was then analyzed by mass spectrometry (LC-MS/MS). A control purified sample standard of DP13 with 99.87 purity (HPLC) and ≥99.5 enantiomeric purity was provided by Alcami Corporation, The Netherlands. The effective calibration range was 0.2 to 200 ng/ml.

Specific Optical Rotation $[\alpha]_D$

The Specific Optical Rotation $[\alpha]_D$ measurements were performed in solution using the sodium D-line at 589.3 nm of a standard Perkin Elmer Polarimeter 343. For the measurement 1 gram of (R)-(+)-5-(p-cyanophenyl)-5,6,7,8-tetrahydroimidazo[1,5-a]pyridine-dihydrogen-phosphate was dissolved in 100 ml of the respective solvent and this solution was transferred in an optical cuvette of 1 decimeter length. The measurement was done at a temperature of 20° C. or 25° C., respectively. The Specific Optical Rotation $[\alpha]_D$ is calculated by the formula 100×a/(1×c) where: α=observed rotation in degrees; 1=cell path length in decimeters; c=concentration in grams per 100 ml.

Elemental Analysis

Elemental analysis was performed on standard equipment (e.g. vario EL cube elemental analyzer) and the values for carbon, hydrogen and nitrogen were determined.

Chiral HPLC

The chiral HPLC was performed on an Agilent 1100 series LC22 instrument with the following column specifications and conditions:
Column: Chiralpack AD-H, granulometry: 5 μm, 250×4.6 mm; n° ADH0CE-TF087
Mobile phase: Ethanol+0.1% diethylamine (DEA)
Detector wavelength: 230 nm
Oven temperature: 25° C.

Flow rate: 0.5 mL/min
Injection volume: 5 µL
Sample preparation: 0.5 mg/mL in Ethanol+0.1% DEA

XRPD

The X-ray powder diffraction studies were performed using a Bruker AXS D2 PHASER in Bragg-Brentano configuration. Using a Cu anode at 30 kV, 10 mA; sample stage standard rotating; monochromatisation by a Kβ-filter (0.5% Ni). Slits: fixed divergence slits 1.0 mm)(=0.61°, primary axial Soller slit 2.5°, secondary axial Soller slit 2.5°. Detector: Linear detector LYNXEYE with receiving slit 5° detector opening. The standard sample holder (0.1 mm cavity in (510) silicon wafer) had a minimal contribution to the background signal. Measurement conditions: scan range 5 to 45° 2theta, sample rotation 5 rpm, 0.5 s/step, 0.010°/step, 3.0 mm detector slit; and all measuring conditions were logged in the instrument control file. As system suitability, corundum sample A26-826-S(NIST standard) was measured daily.

The software used for data collection was Diffrac Commander v2.0.26. Data analysis was done using Diffrac.Eva v1.4. No background correction or smoothing was applied to the patterns.

Single Crystal X-Ray Analysis

Single crystals of (R)-(+)-5-(p-cyanophenyl)-5,6,7,8-tetrahydroimidazolium[1,5-a]pyridine-dihydrogen-phosphate were grown using a n-propanol/water mixture as solvent. A suitable single crystal was taken out of the mother liquor, immediately coated with high viscosity oil, cut to size and mounted on a Mitagen Microloop and shock frozen to 150 K. The measurement was performed on a Bruker D8 Quest instrument with MoKα radiation, using φ-scans and ω-scans. The molecular structure was subsequently solved by direct method (SHELXT software). All non-hydrogen atoms were refined with anisotropic temperature factors. On the completed model, Bijovoet analysis was performed to determine the absolute configuration.

TGA/DSC

The thermogravimetric analysis and differential scanning calorimetry (TGA/DSC) studies were performed using a Mettler Toledo TGA/DSC1 STARe System with a 34-position auto sampler. The samples were made using Al crucibles (40 µL; pierced). Typically 5-10 mg of sample was loaded into a pre-weighed Al crucible and was kept at 30° C. for 5 minutes, after which it was heated at 10° C./min from 30° C. to 350° C. A nitrogen purge of 40 ml/min was maintained over the sample. The software used for data collection and evaluation was STARe Software v12.10 build 5937. No corrections were applied to the thermogram.

DSC

The DSC studies were performed using a Mettler Toledo DSC1 STARe System. The samples were made using Al crucibles (40 µL; pierced). Typically 1-8 mg of sample was loaded onto a pre-weighed Al crucible and was kept at 30° C. for 5 minutes, after which it was heated at 10° C./min from 30° C. to 350° C. and kept at 350° C. for 1 minute. A nitrogen purge of 40 ml/min was maintained over the sample. As system suitability check Indium and Zinc were used as references. The software used for data collection and evaluation was STARe Software v12.10 build 5937. No corrections were applied to the thermogram.

DVS

The Dynamic Vapour Sorption (DVS) studies were performed using a Surface Measurement Systems Ltd. DVS-1 No Video. The sample was loaded into a balance pan, typically 20-30 mg, and equilibrated at 0% RH. After the material was dried, the RH was increased with 10% per step for 1 hour per increment, ending at 95% RH. After completion of the sorption cycle, the sample was dried using the same method. The software used for data collection was DVSWin v3.01 No Video. Data analysis was performed using DVS Standard Analysis Suite v6.3.0 (Standard).

Solubility

The solubility was determined using the shake-flask method; the solubility was visually determined at 20° C. The listed solvents were added stepwise to 10 mg of compound, with 15 minutes in between additions, until complete dissolution was obtained or a solubility of less than 0.05 mg/ml was reached.

High Throughput Experimentation

High throughput experimentation was performed in well-plate format using a Freeslate Core Module 2 in crystallization configuration equipped with a Julabo FPSO for temperature control of the cooling crystallization experiments.

Solid Dispense System

Solids were dispensed using a Freeslate Core Module Protégé Solid Dispense System in classic and SV-hopper configuration with a Sartorius balance. Hoppers that were used were 25 ml classic hoppers with 8 mm valve size and 4 to 3 mm funnel size, 10 ml classic hoppers with 8 mm valve size and 4 to 3 mm funnel size and SV hoppers with standard 4 ml glass vials.

Racemic 5-(p-cyanophenyl)-5,6,7,8-tetrahydroimidazo[1,5-a]pyridine

The title compound (fadrozole) may be prepared e.g., according to the procedure described by L. J. Browne et al. (J. Med. Chem. 1991, 34, 725.) or obtained by commercial suppliers such as Sigma-Aldrich.

Example 1

Once Daily Administration of DP13

DP13 is abbreviated herein referring to the dihydrogen phosphate salt of (R)-(+)-5-(p-cyanophenyl)-5,6,7,8-tetrahydroimidazo[1,5-a]pyridine. The synthesis of the dihydrogen phosphate salt of (R)-(+)-5-(p-cyanophenyl)-5,6,7,8-tetrahydroimidazo[1,5-a]pyridine is described in Examples 6 and 7 herein. Further reference is made to Applicant's application PCT/EP2017/077511, which is incorporated herein by way of reference.

We have discovered that DP13 administered at oral doses of 4, 8, and 16 mg once daily effectively suppresses plasma aldosterone levels in normal men compared to pretreatment values and placebo-treated control values (Table 1). Responses of 24 normal individuals to DP13 at oral doses of 4, 8, and 16 mg once daily (8 subjects/dose) were evaluated, and their plasma aldosterone and potassium responses were compared to each other and 8 placebo-treated individuals. At all the time points at which aldosterone concentrations were measured, the 8 and 16 mg dose significantly suppressed the concentrations compared to both pretreatment and placebo control values. Twenty-four hours after the last dose of DP 13 on day 8, the 8 and 16 mg doses had suppressed plasma aldosterone by 32% and 50% compared to pretreatment values, respectively.

These data demonstrate that once daily dosing with DP 13 can effectively suppress plasma aldosterone levels in normal individuals possessing a normal functioning renin-angiotensin-aldosterone-feedback system.

TABLE 1

Plasma levels of Aldosterone

Single Ascending Dose (1, 2 mg)

| | Pretreatment | DP13 Treatment | | |
|---|---|---|---|---|
| | Day 1, 08:00 h | Day 1, 14:00 h | Day 1, 20:00 h | Day 2, 08:00 h |
| Placebo | 230 ± 17.7 | 418 ± 52.3 | 306 ± 48.0 | 289 ± 24.6 |
| 1 mg | 171 ± 8.1 | 118 ± 8.4$^e$ | 104 ± 4.9$^e$ | 141 ± 14$^e$ |
| 2 mg | 203 ± 13.8 | 129 ± 8.8$^e$ | 114 ± 9.2$^e$ | 124 ± 9$^e$ |

Multiple Ascending Dose (4, 8, 16 mg)

| | Pretreatment | DP13 Treatment | | |
|---|---|---|---|---|
| | Day 1, 08:00 h | Day 2, 08:00 h | Day 8, 14:00 h | Day 9, 08:00 h |
| Placebo | 259.9 ± 55.3 | 364.2 ± 56.1 | 422.8 ± 67.5 | 280.0 ± 48.8 |
| 4 mg | 306.2 ± 59.0 | 198.4 ± 43.4$^{b,d}$ | 166.2 ± 17.9$^{c,d}$ | 334.9 ± 53.3 |
| 8 mg | 271.4 ± 31.5 | 118.0 ± 12.4$^{b,d}$ | 91.9 ± 7.5$^{c,d}$ | 186.4 ± 22.1$^d$ |
| 16 mg | 314.6 ± 48.6 | 108.4 ± 13.4$^{b,d}$ | 100.9 ± 8.3$^{c,d}$ | 156.0 ± 26.8$^{a,d}$ |

Values are the mean ± SEM (pmol/L)
$^a$p ≤ 0.05 compared to placebo value on day 9 at 08:00 h
$^b$p ≤ 0.05 compared to placebo value on day 2 at 08:00 h
$^c$p ≤ 0.05 compared to placebo value on day 8 at 14:00 h
$^d$p ≤ 0.05 compared to pretreatment values
$^e$p < 0.05 compared to placebo value The oral dose of 4 mg/day of DP13 failed to lower the plasma aldosterone level below the level of the placebo control on day 9 twenty-four hours after the last of 8 daily doses. This failure is attributable to the significant increased plasma potassium levels apparent on day 8 (0800 h) pre-dose (Table 2). The plasma potassium increased in response to the decreased exchange of potassium for sodium by the kidney tubules resulting from the reduced aldosterone at earlier time points leading up to day 8; and increases in circulating potassium stimulate aldosterone synthesis. The two higher doses of DP13, 8 and 16 mg are even potent enough to maintain the suppression of plasma aldosterone even on day 9, 24 hours after the last dose on day 8 in the presents of the increased circulating potassium (Table 2). These data show that DP13 at the given once daily administered doses can suppress aldosterone levels for a longer time and duration even in the presence of increasing circulating potassium levels which are known to exert a compensatory stimulation of aldosterone synthesis.

TABLE 2

Blood levels of potassium prior to DP13 on day 1 and day 8.

| | Pretreatment Day 1, 08:00 h | DP13 Treatment Day 8, 08:00 h |
|---|---|---|
| Placebo | 4.4 ± 0.7 | 4.1 ± 0.8$^a$ |
| 4 mg | 4.4 ± 0.6 | 4.8 ± 0.8$^{a,b}$ |
| 8 mg | 4.3 ± 0.07 | 4.6 ± 0.09$^{a,b}$ |
| 16 mg | 4.4 ± 0.11 | 4.7 ± 0.06$^{a,b}$ |

Values are the mean ± SEM (mmol/L)
$^a$p ≤ 0.01 compared to placebo value
$^b$p ≤ 0.01 compared to pretreatment values Example 2

Plasma Levels of Aldosterone Following ACTH Administration

To demonstrate that doses of DP13 given once daily have the potential to suppress the elevated autonomously secreted aldosterone as seen in PA patients, ACTH was administered exogenously to the same 32 normal individuals evaluated above. The ACTH was administered intravenously (i.v.) on day 7 of DP13 two hours after the 08:00 h daily dose of DP13, and the blood samples for aldosterone measurements were drawn 1 hour after the ACTH and compared to that of a blood sample withdrawn one-half hour prior to the ACTH (one and a half hours post DP13 administration. This process termed the "ACTH stress test", demonstrated that oral doses of either 4, 8, or 16 mg of DP13 given once daily were able to prevent the 2- to 3-fold increases in aldosterone elicited by ACTH in individuals only receiving daily doses of placebo (Table 3). The placebo group's plasma aldosterone concentrations in response to ACTH ranged from 432 to 825 pmol/L. These values are comparable to the range published for PA patients, 359 to 997 pmol/L (Amar et al., 2010, op. cit.).

In the single-dose portion of this study, even a dose as low as 1 mg inhibited the ACTH-stimulated aldosterone response (Table 4).

TABLE 3

Plasma levels of Aldosterone following ACTH administration 10:00 h on day 7

| | Pre-ACTH Day 7, 09:30 h | Post-ACTH Day 7, 11:00 h |
|---|---|---|
| Placebo | 244.1 ± 24.7 | 625.9 ± 55.5$^a$ |
| 4 mg ALDO | 203.5 ± 26.7 | 181.1 ± 14.3$^b$ |
| 8 mg ALDO | 121.0 ± 14.0 | 115.5 ± 10.6$^b$ |
| 16 mg ALDO | 102.2 ± 13.4 | 103.4 ± 11.1$^b$ |

Values are the mean ± SEM (pmol/L)
$^a$p ≤ 0.05 compared to pretreatment value
$^b$p ≤ 0.05 compared to placebo value

TABLE 4

Plasma levels of aldosterone following ACTH administration after a single dose of DP13.

|  | Pre-ACTH Day 1, 09:30 h | Post-ACTH Day 1, 11:00 h | Difference |
|---|---|---|---|
| Placebo | 122 ± 11 | 313 ± 62[b] | 191 |
| 1 mg | 99 ± 13 | 94 ± 6[a] | (−6) |
| Placebo | 171 ± 39 | 514 ± 176[b] | (+343) |
| 2 mg | 132 ± 22 | 120 ± 20[a] | (−12) |

Values are the mean ± SD (pmol/L)
[a] $p < 0.05$ compared to placebo
[b] $p < 0.05$ compared to Pre-CTH
N = six per group

Example 3

Pharmacokinetic Data of the Once Daily Dosing

The once-daily dosing is supported by the pharmacokinetic data describing an elimination half-life for DP13 as determined on day 1 and day 8 of dosing with the means for each dose ranging from a low 8.47 on day 1 at the 4 mg dose to 9.67 measured on day 8 at the 16 mg dose Table 5. The $AUC_{0-t}$, $C_{max}$, $T_{max}$ and $T_{1/2}$ for the 1 and 2 mg dose of DP13 were determined in a single dose pharmacokinetic study (Table 5).

TABLE 5

Summary of pharmacokinetic parameters on the first and last day of DP13 dosing

| Dose | Day | $AUC_{0-t}$ (ng·h/mL) | $AUC_{0-\infty}$ (ng·h/mL) | $C_{max}$ (ng/mL) | $T_{max}$ (h) | $T_{1/2}$ (h) |
|---|---|---|---|---|---|---|
| 1 mg | 1 | 45.8 ± 4.16 |  | 4.68 ± 0.38 | 2.00 ± 0.49 | 8.19 ± 0.43 |
| 2 mg | 1 | 133 ± 27.41 |  | 12.0 ± 1.71 | 2.08 ± 0.36 | 11.3 ± 1.28 |
| 4 mg | 1 | 139 ± 15.0 | 167 ± 22.0 | 14.0 ± 1.6 | 2.08 ± 0.28 | 8.47 ± 1.0 |
| 4 mg | 8 | 154 ± 20.5 | 154 ± 20.5 | 15.1 ± 1.1 | 1.92 ± 0.35 | 8.58 ± 1.1 |
| 8 mg | 1 | 281 ± 24.2 | 335 ± 31.5 | 29.4 ± 2.5 | 1.81 ± 0.25 | 8.82 ± 0.4 |
| 8 mg | 8 | 338 ± 28.5 | 338 ± 28.5 | 37.9 ± 3.9 | 1.56 ± 0.26 | 8.92 ± 0.5 |
| 16 mg | 1 | 610 ± 34.7 | 740 ± 65.8 | 66.8 ± 6.1 | 1.88 ± 0.41 | 9.04 ± 0.8 |
| 16 mg | 8 | 725 ± 51.4 | 725 ± 51.4 | 77.4 ± 6.9 | 1.88 ± 0.40 | 9.67 ± 1.0 |

TABLE 6

| Dose | Day | $AUC_{0-tau}$ (ng·h/mL) |
|---|---|---|
| 4 mg | 1 | 134 ± 29.2 |
| 4 mg | 8 | 148 ± 33.0 |
| 8 mg | 1 | 274 ± 24.9 |
| 8 mg | 8 | 331 ± 22.5 |
| 16 mg | 1 | 603 ± 15.8 |
| 16 mg | 8 | 714 ± 19.1 |

Values are the geometric means ± geometric coefficient of variation (CV %)

Both the $C_{max}$ and $AUG_{0-\infty}$ for all dose levels were dose-proportional. The $T_{max}$ shows that the drug was absorbed rapidly at all dose levels and is comparable at day 1 and day 8. On Day 8, there was little accumulation of DP13 in plasma with a geometric mean accumulation ratio ($RA_{Obs}$) of 1.18 for $AUC_{0-tau}$ (individual range: 1.04 to 1.31).

Example 4

Cortisol Concentrations in Response to ACTH Stimulation

Once a day dosing may have a particular advantage as it relates to aldosterone synthase inhibitors. Aldosterone synthase (CYP11B2) shares 95% identity with the coding regions with the gene for CYP11B1, which like CYP11B1 is capable of converting 11β-deoxycorticosterone (DOC) to corticosterone. As a consequence of the genetic coding similarities of these two 11-β hydroxylating enzymes, it has been difficult to-date to identify compounds totally selective for inhibition of aldosterone synthase (CYP11B2). Therefore, aldosterone synthase inhibitors identified to-date inhibit to various degrees both CYP11B1 and CYP11B2 which results in increases in the substrates for these enzymes, particular DOC, DOC is a mineralocorticoid that shares the same pharmacological activities of aldosterone and like aldosterone can alter sodium and potassium homeostasis and raise blood pressure when present at levels well above its normal plasma concentration (Baxter et al., J. Clin. Invest. (1976) 58:579). Patients with hypertension and low plasma renin activity secondary to 11β- or 17-hydroxylase deficiency have elevated DOC levels greater than 10 times normal levels and this elevation appears to be responsible for the hypertension experienced by these patients (Brown and Strott, J. Clin. Endocr. (1971).

As demonstrated above, half-life of DP13 supports once-daily dosing. Thus, it may prove more efficacy because of its only low production of DOC as supported by the data of presented herein (Table 7). DP13 raised DOC levels at all the doses both compared to placebo and pretreatment levels (Table 7). However, unlike with LCI699, DOC increase induced by once daily administration of DP13 was rather low. LCI699 at doses of 0.5 and 1.0 mg taken twice a day decreased plasma aldosterone by 70-80% in PA patients, but increased DOC over 700% to a mean level of 9.8 ng/ml with individual levels ranging from 8.0 to 120.4 ng/ml at the 1.0 mg twice-daily dose (Amar et al., Hypertension (2010) 56:831). In contrast, the highest mean increase in DOC was only 0.52 ng/ml, nearly 20-fold less than seen with LCI699, and the highest individual value was 1.92 ng/ml, over 50-fold less than seen with LCI699. The DOC concentrations observed with DP13 are well below the critical range, 5-7 ng/ml, expected to exert significant mineralocorticoid activity (Amar et al., Hypertension (2010) 56:831).

Because of the potential dual inhibition of both CYP11B1 and CYP11B2 with aldosterone synthase inhibitors, there is concern that inhibition of CYP11B1 might result in a deficiency in the adrenal glands' cortisol secretory response necessary to meet the demands of a stressful situation. The ACTH (Synacten) stress test as describes earlier is the standard measure for evaluating the normalcy of the response. An ACTH stimulated response elevating cortisol concentrations to a value at or above 552 nmol/L is predictive of a normal response to the stress of general anesthesia and major surgery (Santen et al., (1989) 68:99). Of the 24 subjects receiving DP13, only one subject had a cortisol value below this level. His value increased from 324 to 504 nmol/L in response to ACTH just below the 552 nmol/L guideline value. This subject had received the highest dose of DP13 (16 mg/day).

TABLE 7

Plasma 11β-deoxycorticosterone (DOC) concentrations [ng/ml] after various days of DP13 treatment.

| | Pretreatment | DP13 Treatment | | |
|---|---|---|---|---|
| | Day 1, 08:00 h | Day 2, 08:00 h | Day 8, 08:00 h | Day 9, 08:00 h |
| Placebo | 0.04 ± 0.01 | 0.05 ± 0.01 | 0.05 ± 0.02 | 0.04 ± 0.02 |
| 4 mg | 0.04 ± 0.01 | 0.07 ± 0.01 | 0.14 ± 0.02$^{c,d}$ | 0.14 ± 0.02$^{a,d}$ |
| 8 mg | 0.06 ± 0.01 | 0.13 ± 0.03$^{b,d}$ | 0.24 ± 0.03$^{c,d}$ | 0.26 ± 0.04$^{a,d}$ |
| 16 mg | 0.05 ± 0.01 | 0.19 ± 0.05$^{b,d}$ | 0.52 ± 0.09$^{c,d}$ | 0.48 ± 0.13$^{a,d}$ |

Values are the mean ± SEM (ng/mL)
$^{a}$p ≤ 0.05 compared to placebo value on day 9 at 18:00 h
$^{b}$p ≤ 0.05 compared to placebo value on day 2 at 08:00 h
$^{c}$p ≤ 0.05 compared to placebo value on day 8 at 08:00 h
$^{d}$p ≤ 0.05 compared to pretreatment values Example 5

Assessment of Aromatase and Aldosterone Synthase Inhibition by (R)-(+)-5-(p-cyanophenyl)-5,6,7,8-tetrahydroimidazolium[1,5-a]pyridine dihydrogen phosphate Human NCI-H295R Cell Assay for Aldosterone Synthase (CYP11B2) and Aromatase (CYP19) Activities NCI-H295R cells, a continuous cell line derived from an invasive primary adrenocortical carcinoma were obtained from CLS cell line services GmbH (catalog No. 300483). Because NCI-H295R cells produce both aldosterone and estradiol, they enable measuring aldosterone synthase activity and aromatase activity under identical conditions. Prior to being used for the assays the cells were maintained in DMEM/Ham's medium with 15 mM HEPES and 1.2 g NaHCO3 supplemented with 5% steroid-free serum replacement, Panexin BMM (PAN Biotech, Aldenbach, Germany; cat. no. PO4-9515A2), 1% Penicillin/Streptomycin, 1.25% L-Glutamine, and 6.25 µg/ml insulin, 6.25 ng/ml selenium, 5.35 µg/ml linoleic acid and 1.25 mg/ml bovine serum albumin. The cells were maintained at 37° C. under an atmosphere of 95% air/5% CO2. For the assays the cells were sub-cultured at a density of 5×105 cells per well in 24-well plates and grown until 50-60% confluency (48 h). The growth medium then was replaced with 500 µl serum-free DMEM:Ham's F12 containing the test compound dissolved in ethanol/water 1:1 (v/v) so that the final concentration in the assay consisted of 0.5% ethanol. Six concentrations were evaluated, and control samples with no compound were supplemented with 0.5% ethanol. The cells with compound were incubated at 37° C. under 95% air/5% CO2 for 6 h. After which the supernatant was removed and stored at −20° C. until analysis. After the supernatant was removed the cells were evaluated to assure viability by optical evaluation utilizing phase contrast microscopy examination for morphological changes and by the resazurin method which measures the conversion of resazurin into a fluorescent end product resorufin. Non-viable cells lack the metabolic capacity to make the conversion. The conversion was quantified by measuring the fluorescence at 544 nm/590 nm (extinction/emission) respectively using a Wallac 1420 Multiple Counter Victor Fluorometer/Luminator (Perkin Elmer, Wlatham, MA).

Quantification of aldosterone concentration as a measure of aldosterone synthase activity was accomplished by LC-MS as follows. Prior to analysis acetonitrile was used to precipitate the sample protein and following centrifugation the particle free supernatant was subject to LC-MS. The HPLC system consisted of an Accela U-HPLC pump and Accela Open auto sampler (Thermo Fisher Scientific, Waltham, MA). Mass spectrometry was performed using a Q-Exactive MS (Orbitrap) equipped with a heated electrospray (H-ESI) interface connected to a PC running the standard Xcalibur software 2.2 (Thermo Fisher Scientific, Waltham, MA). The LC was performed in the gradient mode using acetonitrile with 0.1% formic acid (solvent A) and aqueous 0.1% formic acid solvent B. The pump flow rate was set to 600 µl/min, and separation was performed on a Kinetex Phenyl-Hexyl 2.6 µm, 50×2.1 mm analytical column (Phenomenex, Germany) with a C6-Phenyl, 4×2.0 mm ID pre-column for quantification. As MS tune file a generic tune file was used and as a lock mass for internal calibration the [M+H]+ ion of the diisooctyl phthalate (m/z 391.28492) present in the solvent system was used. Full MS-SIM analysis (m/z: 250-400) was applied with the mass resolution of the Orbitrap™ set to 35,000. The sample injection volume was 20 µl for all samples. The results were displayed as ng/ml and inhibition of aldosterone production was expressed as percent inhibition relative to untreated controls i.e., in absence of any inhibitor (Table 8). IC$_{50}$ values were calculated using linear interpolation using the concentrations of test compound and the corresponding percentage inhibition that are immediately above and below 50% as illustrated below:

$$IC_{50} = (50\% - Low_{inh}\%)/(High_{inh}\% - Low_{inh}\%) \times (High_{conc} - Low_{conc}) + Low_{conc}$$

where "inh" is inhibition and "conc" is concentration.

TABLE 8

Inhibition of aldosterone production by (R)-(+)-5-(p-cyanophenyl)-5,6,7,8-tetrahydroimidazolium[1,5-a]pyridine dihydrogen phosphate in NCI-H295R cells.

| Concentration (nM) | Mean Inhibition (%) - 3 determinations | Standard Deviation |
|---|---|---|
| 10'000 | 100.0 | 0.0 |
| 1'000 | 100.0 | 0.0 |
| 100 | 100.0 | 0.0 |
| 10$^{a}$ | 60.8$^{c}$ | 4.0 |
| 1$^{b}$ | 8.7$^{d}$ | 13.0 |
| 0.1 | −19.6 | 9.9 |

$^{a}$High$_{conc}$ = the lowest concentration of the test item that inhibits by at least 50% (10 nM);
$^{b}$Low$_{conc}$ = the highest concentration of the test item that inhibits less than 50% (1 nM);
$^{c}$High$_{inh}$ = percent inhibition achieved at the High$_{conc}$ of the test item (60.8%);
$^{d}$Low$_{inh}$ = percent inhibition achieved at the Low$_{conc}$ of the test item (8.7%);
IC$_{50}$ = (50% − 8.7%)/(60.8% − 8.7%) × (10 nm − 1 nM) + 1 nM = 8.1 nM;
IC$_{50}$ = 8.1 nM for inhibition of aldosterone production (aldosterone synthase activity)

Aromatase activity was measured by quantification of the estradiol concentration in the supernatant from incubation of NCI-H295R cells as described above for determination of aldosterone synthase activity except that much higher concentrations of the inhibitor, as indicated below were used to obtain an IC50. Quantification of estradiol concentration was accomplished using a 17-beta-estradiol ELISA kit from IBL-Hamburg (Hamburg, Germany) according to the manufacturer's instructions. A standard curve was generated by plotting the absorbance of each reference standard (y-axis) against the corresponding log concentration (x-axis). The absorbance of each sample was used to determine the corresponding values by interpolation from the standard curve using GraphPad Prism 5.04 software (GraphPad Software Inc., San Diego, CA).

The $IC_{50}$ was calculated herein using the formula described above for the aldosterone synthase data disclosed in Table 9.

TABLE 9

Inhibition of estradiol production by (R)-(+)-
5-(p-cyanophenyl)-5,6,7,8-tetrahydroimidazolium[1,5-
a]pyridine dihydrogen phosphate in NCI-H295R cells

| Concentration (nM) | Mean Inhibition (%) - 3 determinations | Standard Deviation |
|---|---|---|
| 1000 | 80.4 | 1.6 |
| 100 | 82.8 | 0.8 |
| 10$^a$ | 68.6$^c$ | 5.3 |
| 1$^b$ | 29.1$^d$ | 8.4 |
| 0.1 | 12.5 | 5.3 |
| 0.01 | −1.5 | 14.8 |

$^a$High$_{conc}$ = the lowest concentration of the test item that inhibits by at least 50% (10 µM);
$^b$Low$_{conc}$ = the highest concentration of the test item that inhibits less than 50% (1 µM);
$^c$High$_{inh}$ = percent inhibition achieved by the High$_{conc}$ of the test item (68.6%)
$^d$Low$_{inh}$ = percent inhibition achieved by the Low$_{conc}$ of the test item (29.1%);
$IC_{50}$ = (50% − 29.1%)/(68.6% − 29.1%) × (10 µM − 1 µM) + 1 µM = 5.76 µM or 5760 nM;
$IC_{50}$ = 5760 nM for inhibition of estradiol production (aromatase activity)

Cell-Free Human Recombinant Aromatase Assay

Aromatase (CYP19) activity was measured using a human CYP19 assay kit (Corning®, Corning, NY; Product #456260) according to the manufacturer's instructions. The assay system utilized a recombinant human enzyme, a fluorometric substrate MFC (7-methyl-4-trifluoro-methyl-Coumarin), and an NADPH regenerating system consisting of glucose-6-phosphate dehydrogenase, NADP$^+$, and glucose-6-phosphate. For determining the concentrations of the test compounds which inhibited the enzyme activity by 50% ($IC_{50}$) eight test concentrations were tested. The test compounds were dissolved in ethanol/water 1:1 (v/v) so that the final ethanol concentration in the assay was 1%. The test compounds at various concentrations along with the NADPH regenerating system were added to 96-well plates. After a 10 min pre-incubation the reaction was started by the addition of pre-warmed enzyme substrate mix and allowed to continue for an additional 30 min at 37° C. The reaction was then stopped by the addition of a solution of 80% acetonitrile and 20% 0.5M Tris base (stop solution). To control for background fluorescence, blank wells (containing no test samples) were also assayed but these wells had the stop solution added prior to the addition of the enzyme substrate mixture. The fluorescent product formed, 7-hydroxy-4-trifluoro-methyl-Coumarine (HFC) was detected using a Wallac 1420 Multiple Counter Victor Fluorometer/Luminator (Perkin Elmer, Wlatham, MA). The wave lengths for excitation and emission were 405 and 535 nm, respectively. The data was compiled with standard software Wallac 1420 Manager 3.0. In addition to subtraction of the blank well samples as indicated above, each test substance was pre-tested for auto-fluorescence. For this purpose the NADPH generating system (cofactor mix) and the enzyme/substrate-mix were replaced by a comparable mixture of control protein, assay buffer, and test compound solvent. These control samples were then pre-incubated and assayed and as described above. Three independent determinations of the $IC_{50}$ were made from line of best fit plots of % inhibition versus inhibitor concentration (Table 10).

TABLE 10

Inhibition of human recombinant aromatase activity
by (R)-(+)-5-(p-cyanophenyl)-5,6,7,8-tetrahydroimidazolium[1,5-
a]pyridine dihydrogen phosphate.

| Trial (8 concentrations of inhibitor per trial) | Half-maximal inhibitory concentration $IC_{50}$ (nM) |
|---|---|
| 1 | 1694 |
| 2 | 1557 |
| 3 | 1668 |
| Mean | 1640 |
| Standard deviation | ±72.5 |

Example 6

Preparation of (R)-(+)-5-(p-cyanophenyl)-5,6,7,8-tetrahydroimidazolium[1,5-a]pyridine dihydrogen phosphate (Crystalline Form I)

Step 1: Preparation of (R)-(+)-5-(p-cyanophenyl)-5,6,7,8-tetrahydroimidazolium[1,5-a]pyridine dibenzoyl-L-tartrate In a 10 L reactor were loaded at 20° C. racemic 5-(p-cyanophenyl)-5,6,7,8-tetrahydroimidazo[1,5-a]pyridine (328 g, =1.0 eq) and ethanol (2.3 L). The mixture was heated to 40° C. then a solution of (−)-O,O'-dibenzoyl-L-tartaric acid (276.4 g, 0.5 eq) in ethanol (1 L) was added. The mixture was maintained at 40° C. for 1 h, then cooled to 20° C. over a period of 2 h, maintained for 1 h at this temperature, then cooled to 10° C. over a period of 0.5 h and finally maintained at 10° C. overnight. The precipitate was subsequently filtered off and the filter cake was washed with cold (0° C.) ethanol (1 L) to afford the title compound as a white humid powder (485 g, =413.7 g estimated dry, by loss on drying, 48.4%, ee=87%).

Step 2: Recrystallization of (R)-(+)-5-(p-cyanophenyl)-5,6,7,8-tetrahydroimidazolium[1,5-a]pyridine dibenzoyl-L-tartrate In a 10 L reactor were loaded at 20° C. (R)-(+)-5-(p-cyanophenyl)-5,6,7,8-tetrahydroimidazolium[1,5-a]pyridine dibenzoyl-L-tartrate (485 g, ee=87%, =413.7 g estimated dry, by loss on drying, =1.0 eq) obtained from step 1, ethanol (10 L, 24 V) and water (2.4 L, 6V). The resulting mixture was heated to reflux, whereupon a solution was formed. The solution was then cooled to 50° C. and maintained at this temperature for 1 h. Subsequently, the mixture was allowed to cool to 10° C. over a period of 2 h and then maintained at this temperature overnight. The precipitate was filtered off and the filter cake was washed with cold (0° C.) ethanol (1.2 L). The product was dried under reduced pressure at 40° C. to afford the title compound as a white powder (294.8 g, 71%, single enantiomer). Enantiomeric Excess: >99.9% as determined by HPLC Step 3: Preparation of (R)-(+)-5-(p-cyanophenyl)-5,6,7,8-tetrahydroimidazo[1,5-a]pyridine (Free Base)

In a 2 L reactor were loaded (R)-(+)-5-(p-cyanophenyl)-5,6,7,8-tetrahydroimidazolium[1,5-a]pyridine dibenzoyl-L-tartrate (177 g, single enantiomer) obtained from step 2 and dichloromethane (1.77 L, 10 V). Then, a solution of $Na_2CO_3$ (71 g, 2.2 eq) in water (875 mL) was added. After 0.25 h stirring at room temperature, the mixture was decanted. The liquid phases thus obtained were limpid and the aqueous phase had a pH of 8-9. The organic phase was washed with water (2×875 mL) and then concentrated under vacuum. The residue was dissolved in ethanol and again concentrated under vacuum to afford the title compound (70 g, quant.) as an oil which solidified upon standing.

Step 4: (R)-(+)-5-(p-cyanophenyl)-5,6,7,8-tetrahydroimidazolium[1,5-a]pyridine dihydrogen phosphate In a 1 L reactor (R)-(+)-5-(p-cyanophenyl)-5,6,7,8-tetrahydroimidazo[1,5-a]pyridine (94 g, 1.0 eq) and ethanol (564 mL) were loaded and the mixture was heated to 35° C. The solution was filtered and the reactor was rinsed with ethanol (94 mL). A solution of $H_3PO_4$ (97 g, 85% wt/wt in $H_2O$) in ethanol (235 mL) was added at the same temperature, rinsing with ethanol (47 mL). After stirring for 1 h at 35° C., the mixture was cooled to 10° C. (at a rate of –20° C./h) and kept at this temperature for 10 h. The resulting solid was filtered off and the filter cake was washed with cold (10° C.) ethanol (3×94 mL). After drying at 50° C. under reduced pressure, the title compound was obtained as a white, crystalline, free flowing powder (100 g, 74%).

XRPD as described in Table 1 and FIG. 7 of Applicant's application PCT/EP2017/077511, the entirety of which is incorporated herein by way of reference. In particular, it should be referred for said XRPD data to Table 1 and FIG. 7 of Applicant's application PCT/EP2017/077511, this specific disclosure is incorporated herein by way of reference.

Melting Point: 189° C. as determined by TGA/DSC and as shown in FIG. 7 of Applicant's application PCT/EP2017/077511, the entirety of which is incorporated herein by way of reference, but in particular, the specific disclosure of said FIG. 7 is incorporated herein by way of reference;

Enantiomeric Excess (ee): >99.9% (as shown in FIG. 3 of Applicant's application PCT/EP2017/077511, the entirety of which is incorporated herein by way of reference, but in particular, the specific disclosure of said FIG. 3 is incorporated herein by way of reference). The chiral HPLC for the determination of the enantiomeric excess of the preparation featured a retention time (tr) of 14.459 min for the R-(+)-enantiomer and 9.814 Min for the S-(–)-enantiomer.

Absolute configuration: R-(+)-on carbon 5 as determined by single crystal X-ray. Specific optical rotation ($CH_3CN$:$H_2O$ 1:1 (v/v)): $[\alpha]_D^{20}$+98.1.

Hygroscopicity: 1.0% at ≥90% relative humidity (RH) as determined by DVS. Water uptake is reversible and crystalline form does not change upon DVS treatment (as shown in FIGS. 4-6 of Applicant's application PCT/EP2017/077511, the entirety of which is incorporated herein by way of reference, but in particular, the specific disclosure of said FIG. 4-6 is incorporated herein by way of reference). Mass loss upon heating up until 225° C. is 1.4% as determined by TGA/DSC (see above). The crystals of (R)-(+)-5-(p-cyanophenyl)-5,6,7,8-tetrahydroimidazolium[1,5-a]pyridine dihydrogen phosphate were further characterized by their elemental analysis, which is in accordance with the values calculated from the molecular formula $C_{14}H_{16}N_3O_4P$ (MW: 321.27): C, 52.4%; H, 5.1%; N, 13.03%.

Example 7

Preparation of (R)-(+)-5-(p-cyanophenyl)-5,6,7,8-tetrahydroimidazolium[1,5-a]pyridine-chloride from (R)-(+)-5-(p-cyanophenyl)-5,6,7,8-tetrahydro-imidazolium[1,5-a]pyridine dihydrogen phosphate via the Free Base (R)-(+)-5-(p-cyanophenyl)-5,6,7,8-tetrahydro-imidazolium [1,5-a]pyridine dihydrogen phosphate (1000 mg, 3.11 mmol,) as prepared in Example 3 was suspended in $Et_2O$ (30 ml) and extracted with saturated aqueous $NaHCO_3$ solution (30 ml). The aqueous layer was extracted with diethyl-ether (2×20 ml) and the combined organic layers were washed with brine (10 ml) and distilled water (10 ml), dried over $Na_2SO_4$, filtered and evaporated to obtain the free base (R)-(+)-5-(p-cyanophenyl)-5,6,7,8-tetrahydroimidazo[1,5-a]pyridine as a white solid which was dried in vacuum over night at 50° C. (530 mg).

Melting point: 101-102° C.; Specific optical rotation (ethanol): $[\alpha]_D^{25}$=+127.3;

The so obtained (R)-(+)-5-(p-cyanophenyl)-5,6,7,8-tetrahydroimidazo[1,5-a]pyridine (100 mg, 0.447 mmol, 1 eq) was dissolved in methylene chloride (2.2 ml) and HCl (2 M in diethylether, 0.34 ml, 0.76 mmol, 1.5 eq) was added and the mixture was stirred for 30 minutes at RT, then evaporated and dried under vacuum at 80° C. (R)-(+)-5-(p-cyanophenyl)-5,6,7,8-tetrahydro-imidazolium[1,5-a]pyridine chloride was isolated as a crystalline solid.

Melting point: 240-243° C.; Specific optical rotation (ethanol): $[\alpha]_D^{20}$ =+104.8; Specific optical rotation ($CH_3CN$:$H_2O$ 1:1 (v/v)): $[\alpha]_D^{20}$=+124.4.

Example 8

Serum Estradiol, Testosterone, and Follicle Stimulating Hormone Concentrations after DP13 Treatment Unlike with fadrozole, as noted above, DP13 neither inhibited estradiol nor increased circulating testosterone or FSH after once-daily oral dosing with 4, 8, or 16 mg. Estradiol was slightly increased at the 4 and 8 mg doses after 8 days of DP13 treatment. Thus, there is no evidence of estrogen suppression (aromatase inhibition) in normal healthy males treated with DP13.

Serum estradiol, testosterone, and follicle stimulating hormone (FSH) levels were measured by Covance's diagnostic unit, Harrogate, UK with the ADVIA Centaur®CP system (Siemens AG). The ADVIA Centaur enhanced estradiol assay is a fully automated, monoclonal, competitive, chemiluminescent immunoassay, and has a sensitivity of 10 pg/ml. The ADVIA Centaur®CP FSH assay is a two-site sandwich immunoassay using direct chemiluminescence technology, which uses two antibodies that have specificity for the intact FSH molecule. The ADVIA Centaur®CP testosterone assay is a competitive, solid phase immunoassay using direct chemiluminescent technology. All of the above assays used for measuring serum estradiol, testosterone, and FSH levels were conducted as described by the manufacture.

TABLE 11

Serum estradiol, testosterone, and follicle stimulating hormone concentrations at various times after DP13 treatment.

| | Pretreatment | Post DP13 treatment | |
|---|---|---|---|
| | Day 1 (08:00 h) | Day 2 (08:00 h) | Day 9 (08:00 h) |
| Estradiol [pM/L] | | | |
| Placebo | 101 ± 18.1 | 97.0 ± 6.4 | 100 ± 8.7 |
| 4 mg | 98 ± 10.2 | 92 ± 9.8 | 127 ± 8.3$^{a,b}$ |
| 8 mg | 90.0 ± 9.5 | 90.0 ± 12.1 | 113 ± 8.3$^{a}$ |
| 16 mg | 97.4 ± 15.3 | 97.0 ± 9.4 | 114.0 ± 8.5 |
| Testosteron [nM/L] | | | |
| Placebo | 18 ± 1.9 | 20 ± 1.4 | 15 ± 1.1$^{a}$ |
| 4 mg | 17 ± 1.9 | 18 ± 1.9 | 15 ± 1.5$^{b}$ |
| 8 mg | 18 ± 1.7 | 21 ± 6.2$^{a}$ | 16 ± 1.4$^{a}$ |
| 16 mg | 17 ± 1.9 | 20 ± 2.0$^{a}$ | 17 ± 1.7 |
| FSH [IU/L] | | | |
| Placebo | 3.5 ± 0.80 | 3.3 ± 0.81 | 3.1 ± 0.78 |
| 4 mg | 2.7 ± 0.22 | 2.7 ± 0.27 | 2.7 ± 0.27 |
| 8 mg | 4.3 ± 0.94 | 4.1 ± 0.79 | 4.1 ± 0.91 |
| 16 mg | 2.6 ± 0.43 | 2.5 ± 0.43 | 2.5 ± 0.43 |

Values are mean ± SEM
$^{a}$p < 0.05 compared to pretreatment
$^{b}$p < 0.05 compared to placebo on same day Further reference is made to PCT/EP2017/077511, the entirety of which is incorporated herein by way of reference and in particular to the Examples and Figures, especially Examples 3-5 and 8.

The invention claimed is:

1. A method of treating a disease or disorder selected from primary aldosteronism and secondary aldosteronism in human a subject in need thereof, the method comprising orally administering once daily to said subject a therapeutically effective amount of a composition comprising 4 mg or 8 mg of a compound which is R)-(+)-5-(p-cyanophenyl)-5,6,7,8-tetrahydroimidazo[1,5-a]pyridine dihydrogen phosphate, wherein said compound has an enantiomeric excess (ee) of the (R) form higher than or equal to 99%.

2. The method according to claim 1, wherein an elimination half-life ($T_{1/2}$) of said compound upon administration of one 4mg or 8mg daily dose to the subject is longer than 8h, as measured in a blood sample of the subject obtained at 8, 12, 16 or 24 hours post-dose.

3. The method according to claim 1, wherein said (R)-(+)-5-(p-cyanophenyl)-5,6,7,8-tetrahydroimidazolium[1,5-a]pyridine dihydrogen phosphate is a crystalline form I of (R)-(+)-5-(p-cyanophenyl)-5,6,7,8-tetrahydroimidazolium[1,5-a]pyridine dihydrogen phosphate, wherein said crystalline form I has an X-ray powder diffraction pattern comprising the following 2θ values measured using CuKα radiation: 19.504; 21.919 and 24.159, wherein each peak may vary by ±0.5.

4. The method according to claim 1, wherein said disease or disorder is primary aldosteronism.

5. The method of claim 1, wherein said disease or disorder is secondary aldosteronism.

6. The method according to claim 1, wherein said compound has an enantiomeric excess (ee) of the (R) form higher than or equal to 99.5%.

7. The method according to claim 1, wherein said compound has an enantiomeric excess (ee) of the (R) form higher than or equal to 99.8%.

8. The method according to claim 1, wherein said compound has an enantiomeric excess (ee) of the (R) form higher than or equal to 99.9%.

9. The method according to claim 1, wherein said disease or disorder is primary aldosteronism, and wherein said composition comprises 8 mg of the compound.

10. The method according to claim 1, wherein said disease or disorder is secondary aldosteronism, and wherein said composition comprises 8 mg of the compound.

11. The method according to claim 1, wherein said disease or disorder is primary aldosteronism, and wherein said composition comprises 4 mg of the compound.

12. The method according to claim 1, wherein said disease or disorder is secondary aldosteronism, and wherein said composition comprises 4 mg of the compound.

13. A method of treating primary aldosteronism in a human subject in need thereof, the method comprising orally administering to the subject 4 mg of the compound (R)-(+)-5-(p-cyanophenyl)-5,6,7,8-tetrahydroimidazolium[1,5-a]pyridine dihydrogen phosphate, once daily, wherein said compound has an enantiomeric excess (ee) of the (R) form higher than or equal to 99%.

14. A method of treating primary aldosteronism in a human subject in need thereof, the method comprising orally administering to the subject 8 mg of the compound (R)-(+)-5-(p-cyanophenyl)-5,6,7,8-tetrahydroimidazolium[1,5-a]pyridine dihydrogen phosphate, once daily, wherein said compound has an enantiomeric excess (ee) of the (R) form higher than or equal to 99%.

15. The method of claim 13, wherein the human subject is a pediatric patient.

16. The method of claim 13, wherein the human subject is a woman of child bearing potential.

17. The method of claim 14, wherein the human subject is a pediatric patient.

18. The method of claim 14, wherein the human subject is a woman of child bearing potential.

* * * * *

UNITED STATES PATENT AND TRADEMARK OFFICE
CERTIFICATE OF CORRECTION

PATENT NO. : 11,992,479 B2
APPLICATION NO. : 17/052359
DATED : May 28, 2024
INVENTOR(S) : Ronald Edward Steele and Christoph Schumacher It is certified that error appears in the above-identified patent and that said Letters Patent is hereby corrected as shown below:

On the Title Page

1. Remove "This patent is subject to a terminal disclaimer."

In the Claims

2. Claim 1, Column 51, Lines 32-34 replace "A method of treating a disease or disorder selected from primary aldosteronism and secondary aldosteronism in human a subject in need thereof, the method comprising" with -- A method of treating a disease or disorder selected from primary aldosteronism and secondary aldosteronism in a human subject in need thereof, the method comprising --

3. Claim 1, Column 51, Lines 37-39 replace "or 8 mg of a compound which is R)-(+)-5-(p-cyanophenyl)-5,6,7,8-tetrahydroimidazo[1,5-a]pyridine dihydrogen phosphate, wherein said compound has an enantiomeric excess" with -- or 8 mg of a compound which is (R)-(+)-5-(p-cyanophenyl)-5,6,7,8-tetrahydroimidazolium[1,5-a]pyridine dihydrogen phosphate, wherein said compound has an enantiomeric excess --

4. Claim 2, Column 51, Lines 41-42 replace the phrase "The method according to claim 1, wherein an elimination half-life ($T_{1/2}$) of said compound upon administration of one 4mg or 8mg daily dose to the subject is longer than" with -- The method according to claim 1, wherein elimination half-life ($T_{1/2}$) of said compound upon administration of one 4mg or 8mg daily dose to the subject is longer than --

5. Claim 3, Column 51, Line 51 to Column 52, Line 3 replace "line form I has an X-ray powder diffraction pattern comprising the following 20 values measured using CuKα radiation: 19.504; 21.919 and 24.159, wherein each peak may vary by ±0.5" with -- line form I has an X-ray powder diffraction pattern comprising the following 2θ values measured using CuKα radiation: 19.504; 21.919 and 24.159, wherein each peak may vary by ±0.5 degrees --

Signed and Sealed this
Twentieth Day of August, 2024

Katherine Kelly Vidal
*Director of the United States Patent and Trademark Office*